United States Patent
Feng et al.

(10) Patent No.: US 9,850,276 B2
(45) Date of Patent: Dec. 26, 2017

(54) BIDENTATE-BINDING MODULATORS OF LRRK2 AND JNK KINASES

(71) Applicant: THE SCRIPPS RESEARCH INSTITUTE, La Jolla, CA (US)

(72) Inventors: Yangbo Feng, Palm Beach Gardens, FL (US); Philip Lo Grasso, Jupiter, FL (US)

(73) Assignee: The Scripps Research Institute, La Jolla, CA (US)

(*) Notice: Subject to any disclaimer, the term of this patent is extended or adjusted under 35 U.S.C. 154(b) by 8 days.

(21) Appl. No.: 14/893,615

(22) PCT Filed: May 22, 2014

(86) PCT No.: PCT/US2014/039190
§ 371 (c)(1),
(2) Date: Nov. 24, 2015

(87) PCT Pub. No.: WO2014/200682
PCT Pub. Date: Dec. 18, 2014

(65) Prior Publication Data
US 2016/0185818 A1    Jun. 30, 2016

Related U.S. Application Data

(60) Provisional application No. 61/827,104, filed on May 24, 2013.

(51) Int. Cl.
| | | |
|---|---|---|
| *C07D 231/56* | (2006.01) |
| *C07D 405/12* | (2006.01) |
| *C07K 5/062* | (2006.01) |
| *C07K 7/06* | (2006.01) |
| *A61K 31/416* | (2006.01) |
| *C07K 5/103* | (2006.01) |
| *A61K 38/00* | (2006.01) |

(52) U.S. Cl.
CPC ........ *C07K 5/06026* (2013.01); *A61K 31/416* (2013.01); *C07D 231/56* (2013.01); *C07D 405/12* (2013.01); *C07K 5/101* (2013.01); *C07K 7/06* (2013.01); *A61K 38/00* (2013.01)

(58) Field of Classification Search
None
See application file for complete search history.

(56) References Cited

U.S. PATENT DOCUMENTS 8,431,529 B2 * 4/2013 Pellecchia ............ C07D 213/56
514/2.9

* cited by examiner

*Primary Examiner* — Kamal Saeed
(74) *Attorney, Agent, or Firm* — Geoffrey K. Cooper; Thomas Fitting

(57) ABSTRACT

Both JNK and LRRK2 are associated with Parkinson's disease (PD), myocardial infarction (MI), and other medical disorders. Here we report a reasonably selective and potent kinase inhibitors (e.g., compounds 6 and 10) that bound to both JNK and LRRK2 (a dual inhibitor). A bidentate-binding strategy that simultaneously utilized the ATP hinge binding and a unique protein surface site outside of the ATP pocket was applied to the design and identification of this kind of inhibitor. Compound 6 was a potent JNK3 and modest LRRK2 dual inhibitor with an enzyme IC50 value of 12 nM and 99 nM (LRRK2-G2019S), respectively. 6 also exhibited good cell potency, inhibited LRRK2:G2019S induced mitochondrial dysfunction in SHSY5Y cells, and was demonstrated to be reasonably selective against a panel of 116 kinases from representative kinase families.

7 Claims, 10 Drawing Sheets

BIDENTATE-BINDING MODULATORS OF LRRK2 AND JNK KINASES

CROSS-REFERENCE TO RELATED APPLICATIONS

This application claims the priority of U.S. provisional application Ser. No. 61/827,104, filed May 24, 2013, and is a United States national phase entry of PCT application serial number PCT/US2014/039190, filed May 22, 2014, the disclosures of which are incorporated herein by reference in their entireties.

STATEMENT OF GOVERNMENT SUPPORT

This invention was made with government support under NS057153 awarded by the National Institutes of Health. The government has certain rights in the invention.

BACKGROUND

The mitogen activated protein (MAP) kinase family member c-jun-N-terminal kinase (JNK) has been shown to be a compelling therapeutic target for a variety of diseases including neurodegeneration, metabolic disorders, inflammation, cardiovascular disease, and cancer. Validation for JNK as a therapeutic target has come from studies employing knock out (KO) mice, peptide inhibitors of JNK and small molecule ATP competitive inhibitors of JNK. The case for JNK as a therapeutic target for cardiovascular disease, and in particular myocardial infarction (MI), is very compelling due to the fact that mitochondrial dysfunction contributes significantly to this disease and JNK is a crucial mediator of cell death signaling via its association with mitochondria in cardiomyocytes both in vitro and in vivo. Indeed, many studies have linked activation of the JNK mitochondrial pathway to cardiomyocyte cell death. For example, it has been shown that jnk1−/− or jnk2−/−, or transgenic mice expressing dominant negative JNK1/2, showed less injury and cellular apoptosis following I/R injury in vivo. The activation of JNK in rabbits subjected to coronary artery ligation followed by reperfusion in vivo as well as in vitro in isolated adult rabbit cardiomyocytes has also been demonstrated. In the latter case, virally expressed dominant negative JNK2 or JNK-interacting protein-1 (JIP) (a 154-amino acid protein substrate competitive inhibitor of JNK) were shown to be protective against simulated I/R in these cell. It has been shown that inhibition of JNK by AS601245 (an ATP competitive inhibitor) decreased cardiomyocyte apoptosis and infarct size in rats after I/R suggesting a therapeutic benefit for JNK inhibition. Since that time, numerous other reports have shown a clear correlation between JNK translocation to the mitochondria and cardiomyocyte death in response to simulated ischemia. For example, primary adult rat cardiomyocytes have been utilized to demonstrate that JNK was activated by oxidative stress and localized to the mitochondria in response to this stress. It has also been shown that inhibiting JNK activation or JNK translocation to the mitochondria with a specific peptide that inhibits JNK-Sab interaction prevents ROS generation, mitochondrial membrane potential dissipation, and cell death.

LRRK2 is a member of the leucine-rich repeat kinase family, and variants of the PARK8 gene which encodes for the enzyme are associated with an increased risk of Parkinson's disease and Crohn's disease. The Gly2019Ser mutation is one of a small number of LRRK2 mutations proven to cause Parkinson's disease.

The design and identification of potent and highly selective JNK and LRRK2 inhibitors has been pursued in the past few years due to potential wide spread therapeutic applications. In particular, development of brain penetrant small molecule inhibitors for JNK and LRRK2 has been a major focus in order to develop efficacious therapeutics for Parkinson's disease (PD) and other neurodegenerative diseases, such as Alzheimer's (AD), Huntington's disease (HD), amyotrophic lateral sclerosis (ALS) and multiple sclerosis (MS). Additionally, inhibition of JNK and/or LRRK2 is believed to be an effective approach for development of therapeutic compounds for treatment of myocardial infarction (MI), obesity, diabetes, Alzheimer's disease, ALS, cancer, rheumatoid arthritis, fibrotic disease, pulmonary fibrosis, kidney disease, liver inflammation, and Crohn's disease.

SUMMARY

The present invention is directed, in various embodiments, to compositions of matter having modulatory bioactivity of kinase enzymes such as JNK isoforms and of LRRK2. These kinases are believed to be involved in medical disorders including Parkinson's disease (PD) Alzheimer's (AD), Huntington's disease (HD), amyotrophic lateral sclerosis (ALS) multiple sclerosis (MS), myocardial infarction (MI), obesity, diabetes, Alzheimer's disease, ALS, cancer, rheumatoid arthritis, fibrotic disease, pulmonary fibrosis, kidney disease, liver inflammation, Crohn's disease, hearing loss, and conditions where modification of feeding behavior is medically indicated, such as Prader-Willi syndrome.

Compounds of the invention are bidentate-binding kinase modulators, that is, the molecules have two moieties, connected by a linker moiety, wherein one moeity binds to a first corresponding domain of the kinase, termed a hinge domain, and the second moiety of the modulator binds to a protein domain of the kinase, termed a surface pocket or peptide-binding pocket. The two moieties of the modulator, which can be an inhibitor of the kinases, are covalently bonded to each other by a linker moiety.

In various embodiments, the invention provides a bidentate kinase inhibitor compound of formula (I) wherein

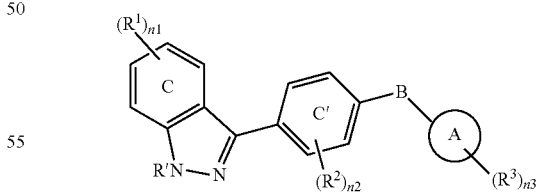

each of ring C and ring C' independently comprises 0, 1, 2, or 3 nitrogen atoms therein; or ring C' is absent, and a direct bond or an ethynyl group bonds ring system C to group B;

group A is a 3-16 membered saturated, partially unsaturated, or aromatic, mono-, bi-, or tricyclic ring system, comprising 0-8 heteroatoms selected from the group consisting of O, N, and $S(O)_q$ wherein q=0, 1, or 2, substituted with n3 $R^3$ groups;

$R^1$, $R^2$, and $R^3$ are each independently at each occurrence OR, $NR_2$, CN, $CF_3$, halo, or a $(C_{1-6})$alkyl optionally comprising therein any of NR', $S(O)_q$, O, C(=S), C(=O), C(=O)O, OC(=O)O, C(=O)C(=O), C(=O)NR', O(C=O)NR' NR'C(=O)NR', SO2NR', or C(=O)NR'NR'; or $R^1$, $R^2$, and $R^3$ are each independently a 3-16 membered saturated, partially unsaturated, or aromatic, mono-, bi-, or tricyclic ring system, comprising 0-8 heteroatoms selected from the group consisting of O, N, and $S(O)_q$ wherein q=0, 1, or 2, substituted with n4 $R^4$ groups;

$R^4$ is independently at each occurrence OR, $NR_2$, CN, $CF_3$, halo, or a $(C_{1-6})$alkyl optionally comprising therewithin any of NR', $S(O)_q$, O, C(=S), C(=O), C(=O)O, OC(=O) O, C(=O)C(=O), C(=O)NR', O(C=O)NR' NR'C(=O) NR', SO2NR', or C(=O)NR'NR';

n1=0, 1, 2, or 3; n2=0, 1, 2, or 3; n3=0, 1, 2, 3, 4, or 5; n4=0, 1, 2, 3, 4, or 5;

R is H, $(C_{1-6})$alkyl, or $(C_{1-6})$acyl;

R' is H, $(C_{1-6})$alkyl, or $(C_{1-6})$acyl; or R' is a 5-16 membered saturated, partially unsaturated, or aromatic, mono-, bi-, or tricyclic ring system, comprising 0-8 heteroatoms selected from the group consisting of O, N, and $S(O)_q$ wherein q=0, 1, or 2, substituted with n4 $R^4$ groups;

B is a linker comprising at least 8 backbone atoms selected from C, N, O, and S(O)q, wherein the linker can be linear or can comprise 1-4 cycloalkyl, heterocyclyl, aryl, or heteroaryl ring systems, any of which is optionally mono- or independently multi-substituted with R';

or a pharmaceutically acceptable salt thereof, or a hydrate, solvate, or prodrug thereof.

The invention also provides, in various embodiments, pharmaceutical compositions and combinations comprising a compound of the invention, as disclosed and claimed herein.

In various embodiments, the invention provides uses of the compound of formula (I) for treatment of a medical disorder in a patient, including Parkinson's disease (PD) Alzheimer's (AD), Huntington's disease (HD), amyotrophic lateral sclerosis (ALS) multiple sclerosis (MS), myocardial infarction (MI), obesity, diabetes, Alzheimer's disease, ALS, cancer, rheumatoid arthritis, fibrotic disease, pulmonary fibrosis, kidney disease, liver inflammation, Crohn's disease, hearing loss, or Prader-Willi syndrome, or a condition where modification of feeding behavior is medically indicated.

DETAILED DESCRIPTION

Overview

Figure 1:
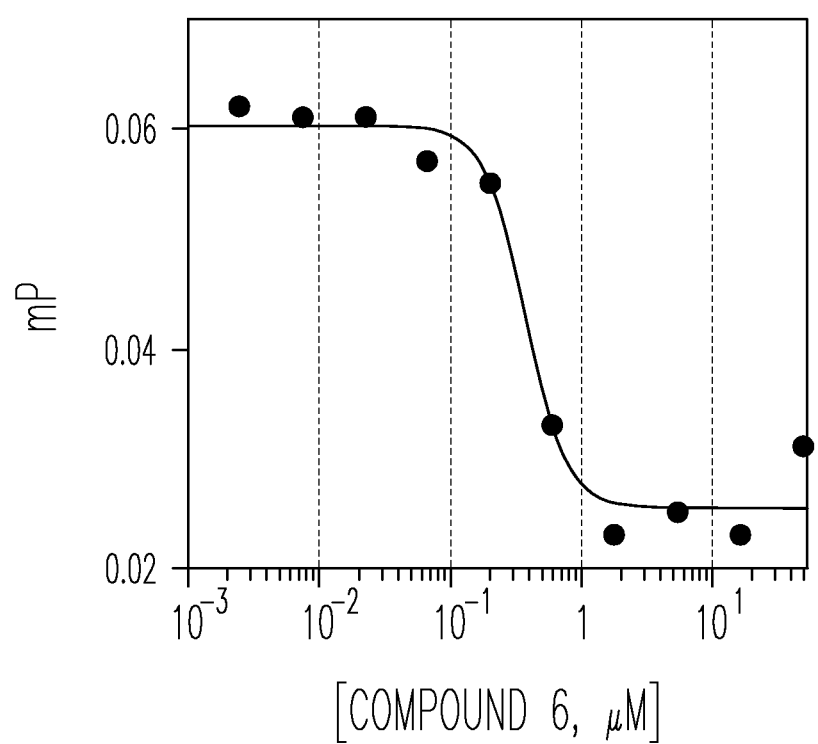
FIG. 1 shows the results of JIP FP displacement assays for compound 6.

We have chosen to develop bidentate JNK and/or LRRK2 inhibitors as therapeutic agents to treat disorders such as Parkinson's disease (PD) Alzheimer's (AD), Huntington's disease (HD), amyotrophic lateral sclerosis (ALS) multiple sclerosis (MS), myocardial infarction (MI), obesity, diabetes, Alzheimer's disease, ALS, cancer, rheumatoid arthritis, fibrotic disease, pulmonary fibrosis, kidney disease, liver inflammation, Crohn's disease, hearing loss, and conditions where modification of feeding behavior is medically indicated, such as Prader-Willi syndrome. The bidentate approach permits the development of inhibitors having a high degree of selectivity, which is expected to afford lower toxicity risk for development candidates for treatment of the conditions associated with JNK and/or LRRK2. In addition, by targeting the substrate site in JNK, and potentially blocking JNK mitochondrial translocation, we may be able to provide an inhibition mechanism that prevents mitochondrial dysfunction and cardiomyocyte cell death. Indeed, the mitochondrial function specific assays presented in this application enable us to monitor several measures of mitochondrial function that contribute to cell death. For example, mitochondrial functional assays measuring ROS and mitochondrial membrane potential (MMP) have not been reported for cardiomyocytes. The robust, high-throughput nature of all these assays can support detailed medicinal chemistry efforts for discovery of novel structural classes and mechanisms of inhibition for JNK. Finally, bidentate inhibitors that do not behave as covalent modifiers and non-covalently bind in the ATP and substrate pockets of JNK have not been reported, and novel structures associated with this approach have been developed.

Compounds have been developed that are capable of inhibiting the bioactivities of both JNK and LRRK2 (dual inhibitors) in the belief that these compounds can exhibit greater efficacy than compounds that inhibited only JNK or LRRK2 individually. Dual inhibitors can be used as in vitro or in vivo probes to test the hypothesis that dual inhibition of JNK and LRRK2 may be additive or synergistic in the treatment of both familial and idiopathic PD and other disorders. A dual inhibitor is preferred over combined, individual JNK and LRRK2 inhibitors because it eliminates complications of drug-drug interactions and the need to optimize individual inhibitor doses for efficacy.

Some kinase inhibitors are ATP-competitive and are called type I inhibitors. The ATP-binding pocket is highly conserved among members of the kinase family and it is difficult to find selective agents. Moreover, the ATP-competitive inhibitors must compete with high intracellular ATP levels leading to a discrepancy between IC50s measured by biochemical versus cellular assays. The non-ATP competitive inhibitors, called type II and type III kinase inhibitors, offer the possibility to overcome these problems. These inhibitors act by inducing a conformational shift in the target enzyme such that the kinase is no longer able to function, as in the DFG-out conformation, the phenylalanine side chain moves to a new position. This movement creates a hydrophobic pocket available for occupation by the inhibitor.

The major challenge in developing kinase inhibitors is to gain high selectivity in order to diminish off-target side effects, which is especially important for non-oncogenic targets such as for CNS applications. Some type-II and type-III kinase inhibitors have given high selectivity since these compounds bind to protein pockets that are unique for a specific kinase, such as the allosteric site for type-III inhibitors and the hydrophobic pocket occupied originally by the Phe residue in the DFG-in conformation for type-II inhibitors. Others, such as BIRB-796 have not been as selective as some type I inhibitors. Additionally, application of type-II and type-III inhibitors can be limited because many kinases cannot assume a DFG-out conformation and allosteric binding sites have been discovered for only a few kinases. The majority of kinase inhibitors developed so far are ATP-competitive and their selectivity can be low due to binding in the highly conserved ATP-binding pocket. Despite this, very selective type-I inhibitors have indeed been developed however.

For each c-jun N-terminal kinase (JNK) isoform, there exists a substrate-binding pocket in proximity to the hinge region of the ATP pocket. Several 11-mer peptides derived from its scaffolding proteins (JNK interacting proteins, JIP) have been demonstrated to be potent substrate-competitive JNK inhibitors (JIP-peptides). See Scheme 1(A), below. Due to the close-proximity of this substrate-binding site to the ATP pocket, a series of potent and selective bidentate-binding JNK1/2 inhibitors composed of the 11-mer JIP-peptides and a hinge binder connected through various linkers have been previously prepared. After optimization, it was found to be possible to reduce the size of the peptide portion from 11-mers to the tri-peptide LNL (compound 1, see Scheme 1(A)). Compound 1, which utilized a 3-phenylindazole as the hinge binder, Region C, and a moiety of propyl-1,3-diamine coupled with a di-Gly as the linker, Region B, still had good potency in both kinase activity assay and JIP displacement assay (Table 1). However, compound 1 and its analogs (with longer peptide moieties) are still peptide-like and possess all the major drawbacks associated with peptide-based drugs.

Starting with the JIP-site-binding tri-peptide moiety in 1 (Ac-LNL-) we replaced this moeity, Region A, with non-peptidic elements in the belief that the resulting bidentate inhibitors would potentially be more drug-like. A series of exploratory studies were embarked on to identify key molecular moieties. As shown in Scheme 1(A), removal of the N-terminal acetyl group to provide compound (2) reduced the JNK3 inhibition (Table 1). The linker length could be shortened from 12 backbone atoms (by replacing the propyl-1,3-diamine coupled with a di-Gly in 1 and 2) to 10 atoms in compound 3 without hurting the JIP displacement activity (Table 1). Several optimization strategies were applied to reduce the peptidic nature of these bidentate inhibitors including addition of a benza-dioxane ring in lieu of the dipeptide (compound 4). This change showed JNK3 inhibition activity and JIP displacement potency, within error, similar to that of 2 and 3 (Table 1). In addition, a peptoid strategy was used to modify one of the Leu residues and the middle Asn residue in the tri-peptide LNL was replaced simply by Gly. More interestingly, the terminal Leu residue could be substituted by a benzamide moiety. It was no surprise that all these modifications were possible since the tri-peptide, LNL, in 1 binds mainly to a hydrophobic pocket in the JIP site.

Here we present a strategy for identifying small molecule kinase inhibitors that combine the advantages of kinase type-I inhibitors (for easy access to kinase inhibitors with high affinity) and the advantages of kinase type-II/III inhibitors (for high selectivity). Specifically, our strategy is to design bidentate-binding inhibitors that can simultaneously bind to the kinase hinge (mimicry of type-I inhibitors) and to a surface pocket close-by but outside of the hinge region and/or the ATP pocket (mimicry of type-II/III inhibitors). This surface pocket could be a substrate binding site or an allosteric binding pocket. The site can be any surface pocket that can provide binding affinity for a small structural element. As long as the selected surface binding site is unique to a specific protein kinase, it is reasonable to assume that the resulting bidentate-binding inhibitors will exhibit high affinity and selectivity, combining hinge binding and surface pocket binding. A schematic representation for this bidentate binding strategy is demonstrated in Scheme 1(B), showing surface pocket binding domain A, linker domain B, and hinge binding domain C of compound 6.

Scheme 1(A)

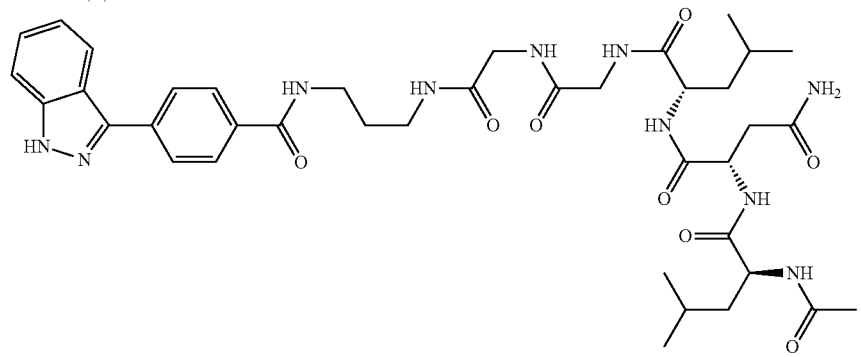

1

-continued
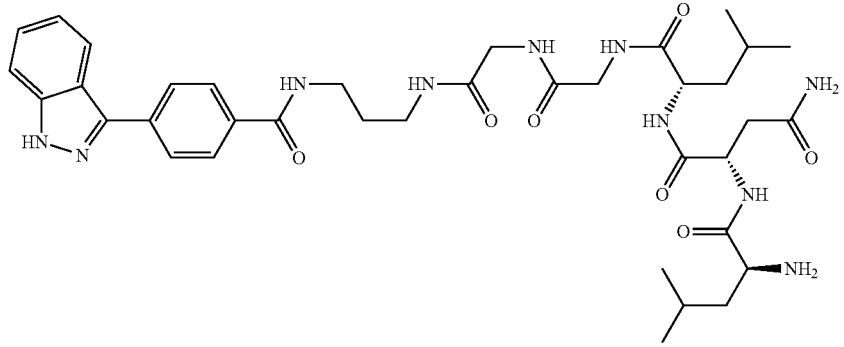
2
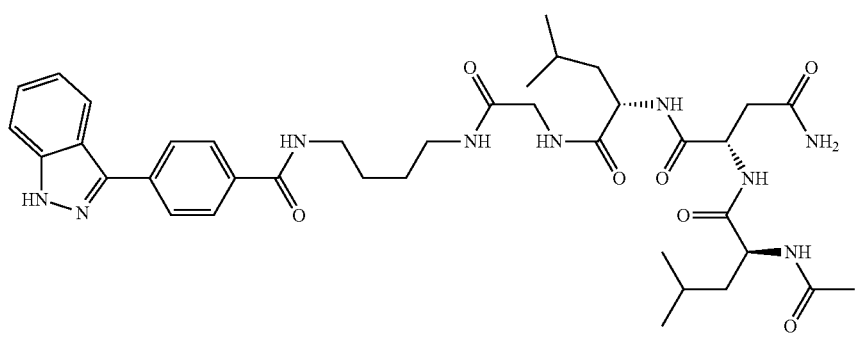
3
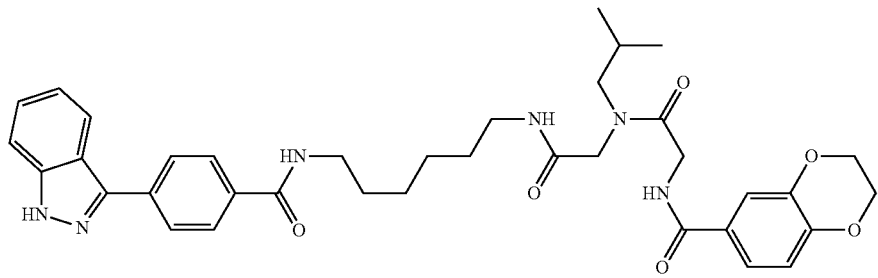
4
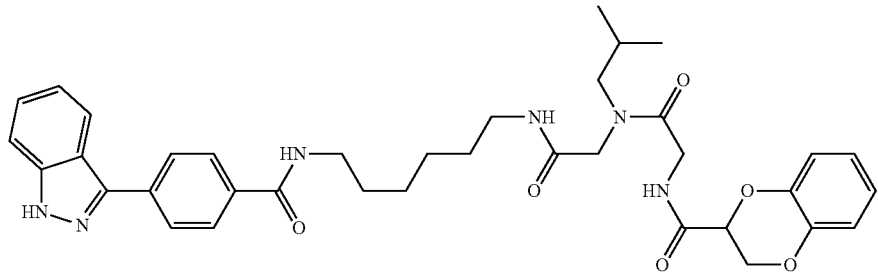
5
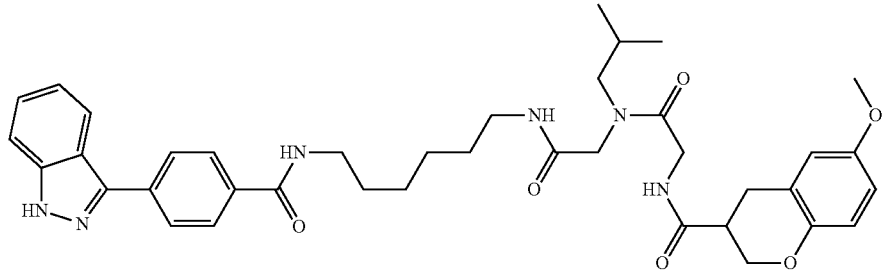
6

7
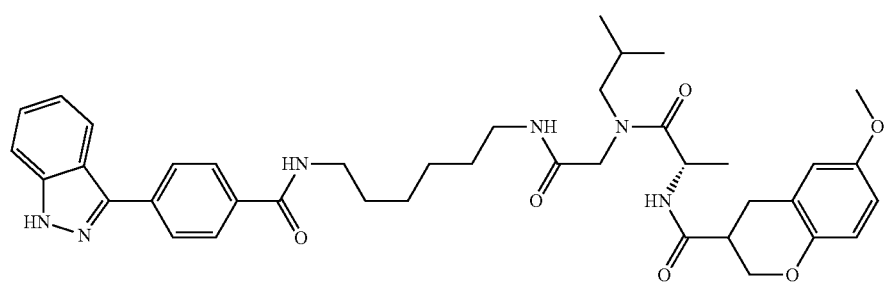
8
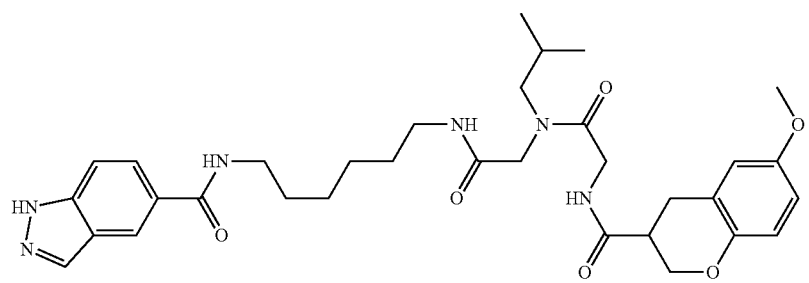
9
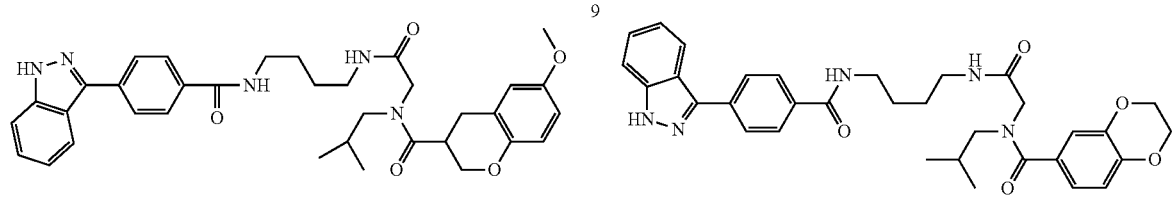
10
11
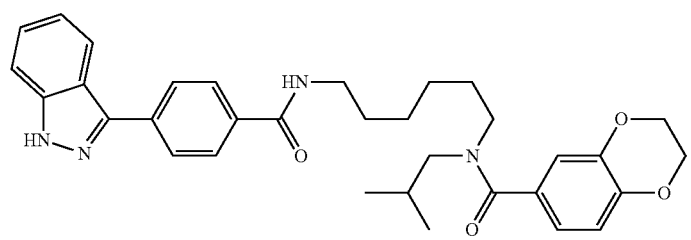
12
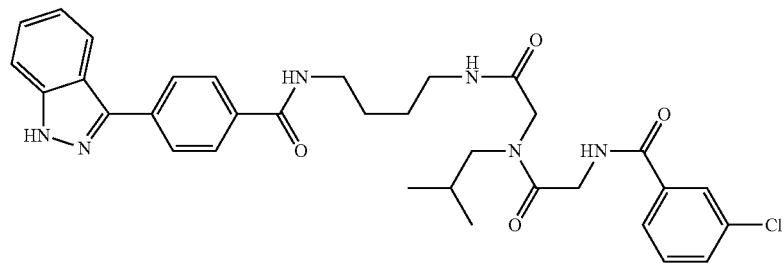

-continued
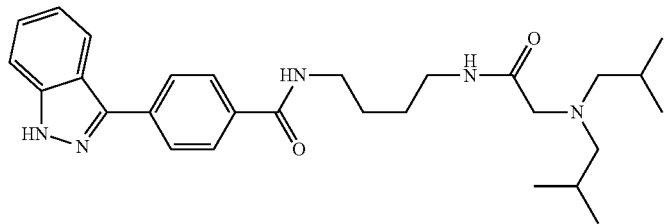
Scheme 1(B)
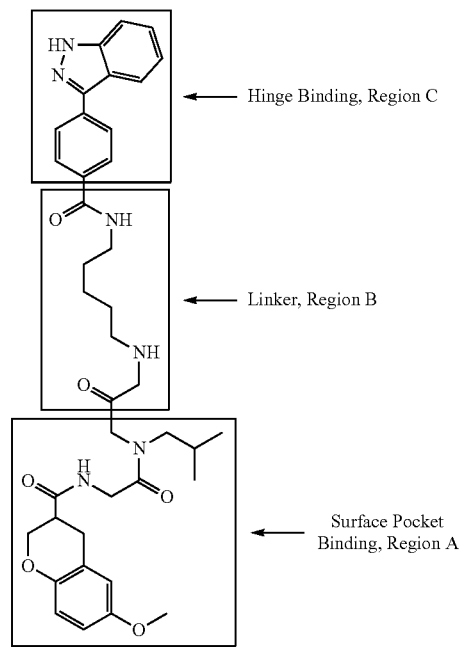
← Hinge Binding, Region C
← Linker, Region B
← Surface Pocket Binding, Region A
Scheme 1(C)
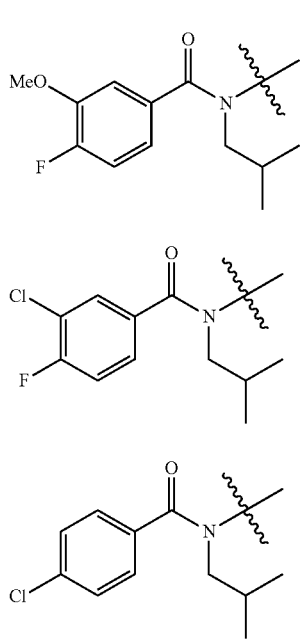
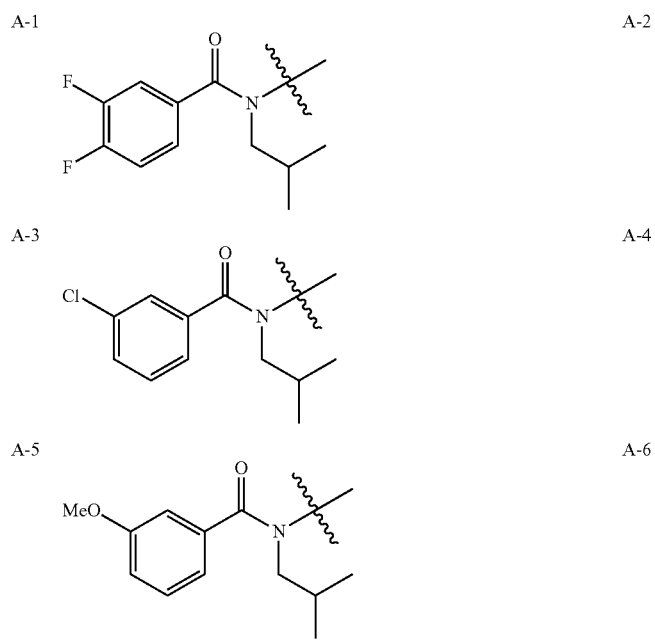

-continued
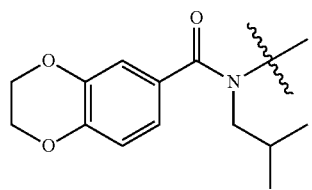
A-7
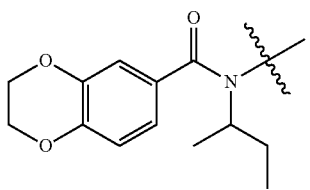
A-8
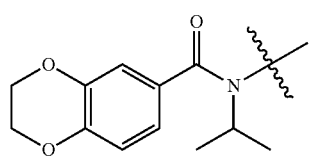
A-9
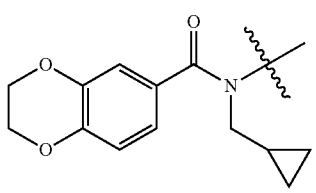
A-10
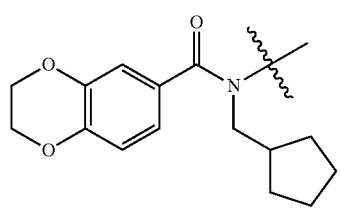
A-11
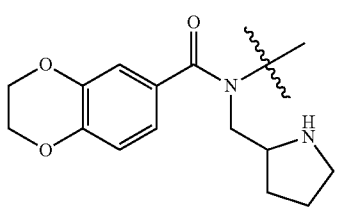
A-12
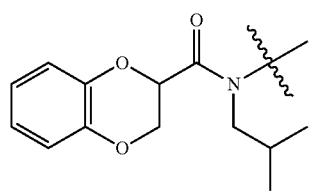
A-13
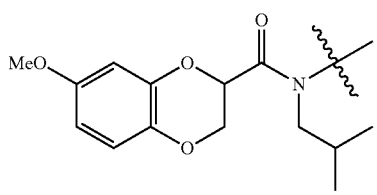
A-14
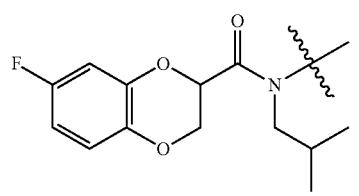
A-15
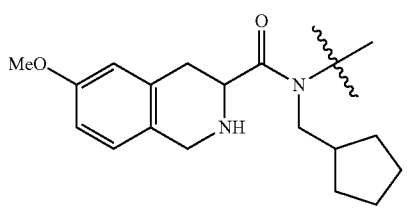
A-16
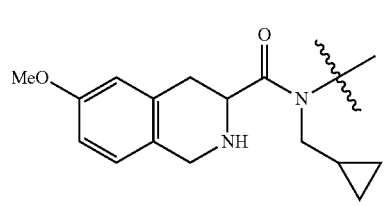
A-17
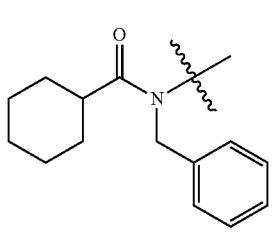
A-18
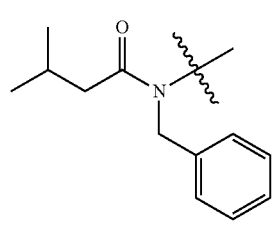
A-19
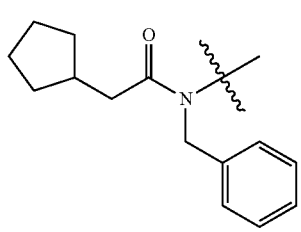
A-20

A-21 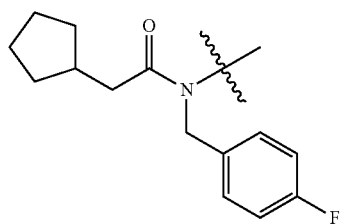
A-22 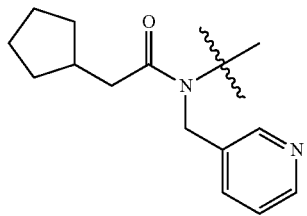
A-23 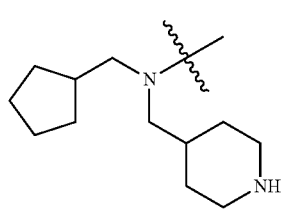
A-24 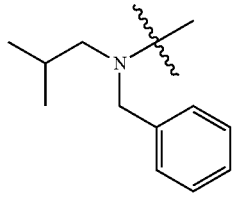
A-25 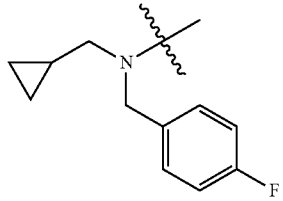
A-26 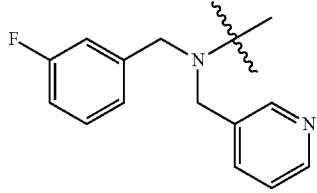
A-27 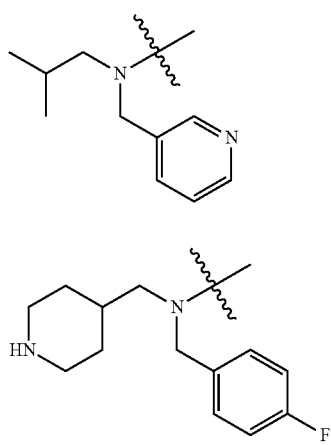
A-28
A-29 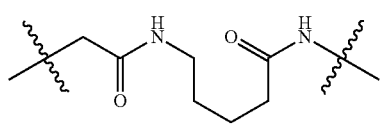
Scheme 1(D)
B-1 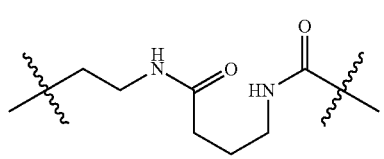
B-2
B-3 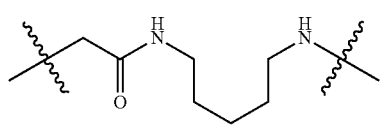
B-4
B-5 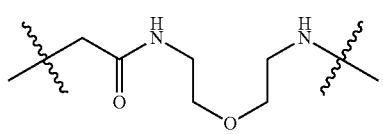
B-6

-continued
| | |
|---|---|
| 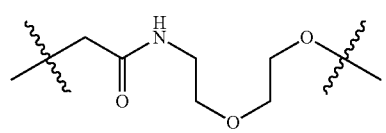 B-7 | 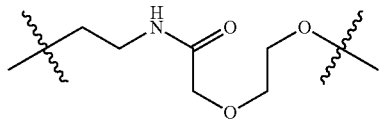 B-8 |
| 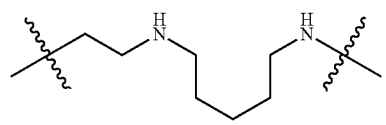 B-9 | B-10 |
| 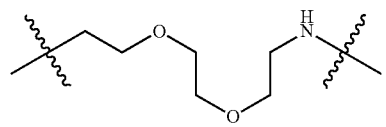 B-11 | 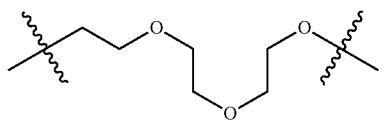 B-12 |
Scheme 1(E)
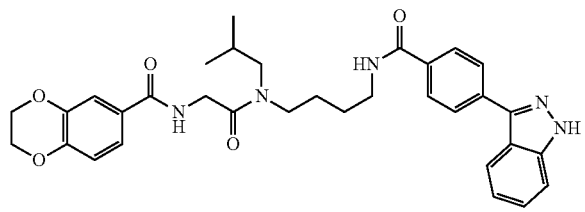
Analog-1 of compound 10
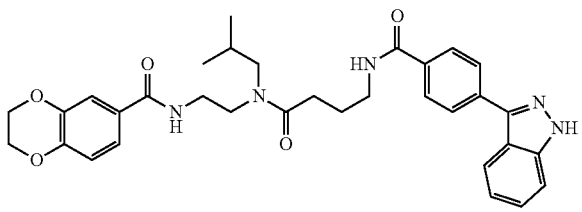
Analog-2 of compound 10
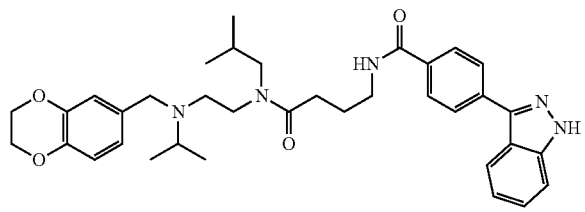
Analog-3 of compound 10
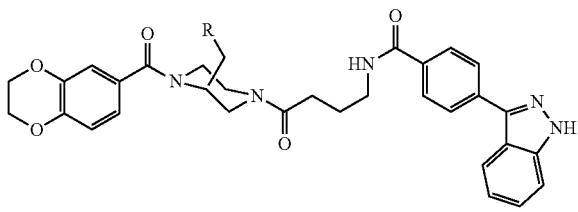
Analog-4 of compound 10
Scheme 1(F)
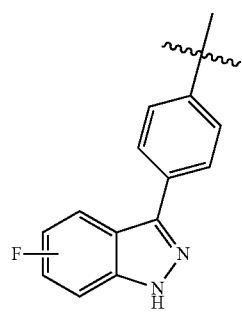
X
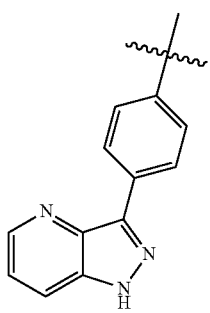
Y -continued

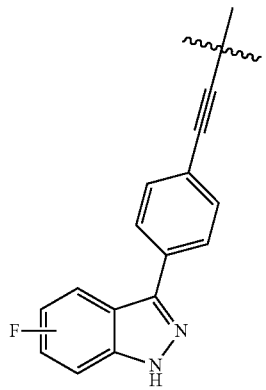

Z

The linker length in 4 was further reduced to 9 backbone atoms and the Gly moiety was totally removed from the linker (Scheme 1(A)), further increasing the small molecule-like nature of the resulting bidentate kinase inhibitors.

TABLE 1

Enzyme assay data for bidentate inhibitors

| Compd. | JNK3 IC$_{50}$ (nM)[a] | JNK1 IC$_{50}$ (nM)[a] | JIP FP displacement IC$_{50}$ (nM)[a] |
|---|---|---|---|
| 1 | 37.8 ± 11.8 | n.d | 760 |
| 2 | 135.5 ± 35.9 | n.d | 624 |
| 3 | 157.5 ± 161.6 | 317.9 ± 11.9 | 620 |
| 4 | 147.4 ± 51.6 | 684.6 ± 121.4 | 907 |
| 5 | 63.4 ± 10.4 | 164.4 ± 21.7 | 363 |
| 6 | 11.6 ± 2.4 | 109.4 ± 6.1 | 336 |
| 7 | 126.7 ± 30.3 | 154.5 ± 37.1 | 1045 |
| 8 | 3154 | n.d | n.d |
| 9* | 246 ± 227 | n.d. | 300 ± 187 |
| 10* | 65 ± 24 | n.d. | 363 ± 272 |
| 11* | 86 ± 37 | n.d. | 781 ± 7 |
| 12* | 184 ± 38 | n.d. | 520 ± 170 |
| 13* | 374 ± 227 | n.d. | 1725 ± 635 |
| SP-600125[b] | 220 ± 42 | 68.0 ± 10.3 | n.d |

[a]IC50 values were calculated from 2-3 determinations.
[b]SP600125, available from Sigma-Aldrich, was used as the positive control JNK inhibitor in our enzyme assays. Data were determined from 10 measurements, except * where n = 2-4.

The most favorable results were obtained when the terminal benzadioxane-6-carboxyl amide in 4 was replaced by its regio-isomer benzadioxane-2-carboxyl amide to give compound 5, which had comparable JNK3 inhibition activity (and a slightly better potency for JNK1) and a better JIP FP displacement potency compared to compound 1. Further optimizations on the terminal bicyclic amide produced the best bidentate-binding kinase inhibitor 6 for this series, where a chroman-3-carboxyl amide was used to displace the benzadioxane amide in Region A. This modification was able to increase the potency (IC$_{50}$ value was 12 nM and 336 nM for JNK3 inhibition and JIP FP displacement, respectively, Table 1). Interestingly, replacement of the Gly in 6 by an Ala residue significantly reduced the potency in both JNK3 and JIP displacement assays (compound 7). Moreover, a series of other hinge binding moieties, Region C, were assessed (such as the 5-yl-indazole in compound 8, Scheme 1(A), Table 1) yet the 3-(4-yl-phenyl)indazole was discovered to be still the best.

The bidentate-binding property of compound 6 and its analogs was demonstrated by the displacement of JIP-peptide in JIP FP assay, and the strong inhibition of JNK activity in the enzyme activity assay (Table 1, JNK inhibition activity). The biochemical assay for JIP displacement is centered on utilizing a TAMRA-JIP-11-mer peptide (TAMRA-RPKRPTTLNLF) with JNK3 39-422 and measuring fluorescence polarization (FP) changes in the presence and absence of small molecule inhibitors. This assay has been established in 96-well and 384-well format in our labs. Unlabeled JIP-peptide (RPKRPTTLNLF, SEQ ID:1) and compound 2 were used as positive controls. The dose-response curve shown in FIG. 1 clearly demonstrated the ability of compound 6 to displace the JIP-peptide with an IC$_{50}$ value of ~336 nM.

The detection method in the JNK3 enzyme assay allows for the detection of a compound that inhibits by a variety of mechanisms including: substrate-site binding, allosteric site binding, and ATP-competitive binding. Assays shown in FIG. 1 already demonstrated the substrate site binding property of compound 6. However, if the inhibition of kinase activity by 6 was only through substrate site binding, its IC$_{50}$ value in JNK3 activity assay should be similar to that in JIP displacement assay. As shown in Table 1, compound 6 (and its analogs) exhibited a much higher potency in JNK3 activity assay than in the JIP displacement assay (12 nM vs. 336 nM), indicating the existence of other interactions in addition to JIP substrate site binding. One possible interaction besides JIP site binding was ATP hinge binding because the head indazole moiety is a well-known hinge binder. Indeed, mechanism of inhibition studies revealed that compound 6 was a competitive inhibitor of ATP showing non-linear fits that are reflective of competitive inhibition and Lineweaver-Burk plots showing the intersecting line pattern representative of an ATP competitive inhibitor. Data were fit to equations for competitive, non-competitive, uncompetitive, and mixed inhibition. χ2 analysis and F-test goodness of fit revealed competitive inhibition for compound 6 (p<0.05).

Figure 2A:
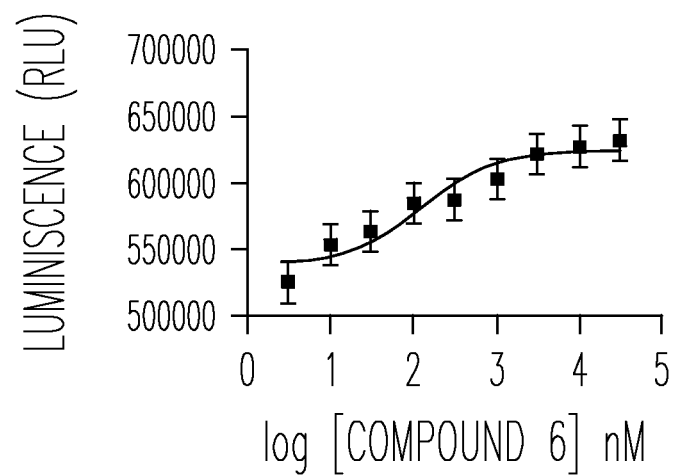
FIG. 2 shows results of enzyme assays for compound 6 in (A): wild-type LRRK2 (IC50: 118 nM); (B): LRRK2-G2019S (IC50: 99 nM).
Figure 2B:
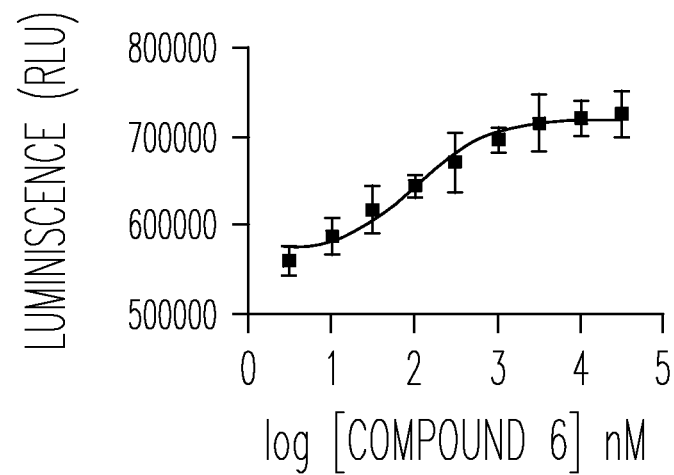

Strong inhibition of LRRK2 by compound 6 was also found. To demonstrate the ability of compound 6 to inhibit the bioactivity of LRRK2, compound 6 was titrated in both wild-type LRRK2 and PD-specific mutant LRRK2-G2019S (FIG. 2), and was found to possess an enzyme inhibition activity of IC$_{50}$~100 nM for both LRRK2 forms. High LRRK2 inhibition was also found for bidentate inhibitors with similar structures to that of compound 6, indicating that there is a general dual inhibition pattern for this series.

Figure 3A:
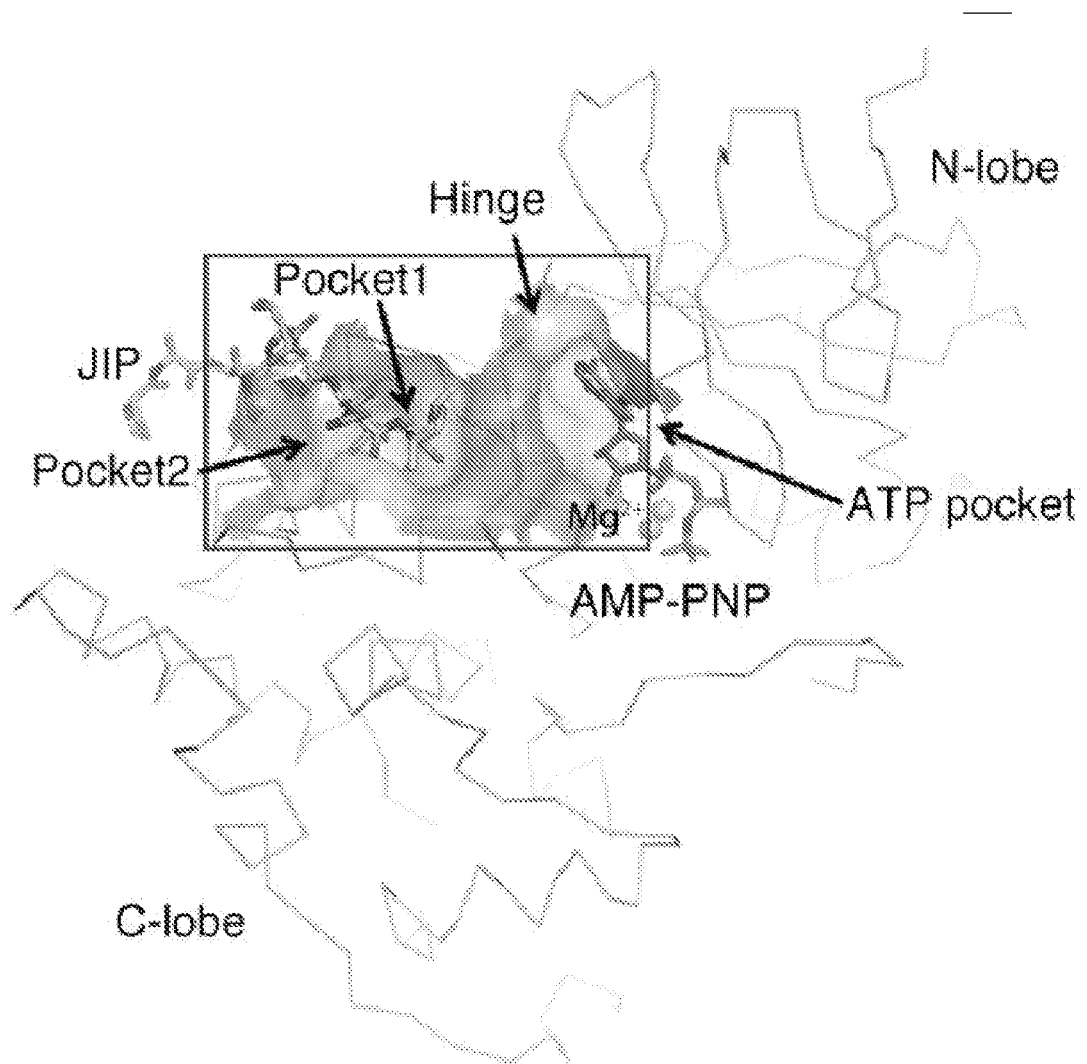
FIG. 3 depicts ribbon representation of the crystal structure of JNK3 in complex with AMP-PCP (PDB ID 1JNK) (A) JIP peptide derived from PDB ID 4H39 is placed to show JIP binding pockets, Pocket1, and Pocket2. N-lobe and C-lobe are colored wheat and light blue, respectively. Ligand binding pockets are shown as a transparent surface with yellow and cyan respectively representing hydrophobic and polar regions. Only the boxed area of each protein is shown in panels B and C. Docking poses of compound 6 to the crystal structure of human JNK3 (B) and a homology model of LRRK2 (C) are shown in sticks with the ligand binding pockets overlaid with transparent surface. Key residues involved in H-bond interactions with 6 are labeled. H-bonds are shown as dashed lines.
Figure 3B:
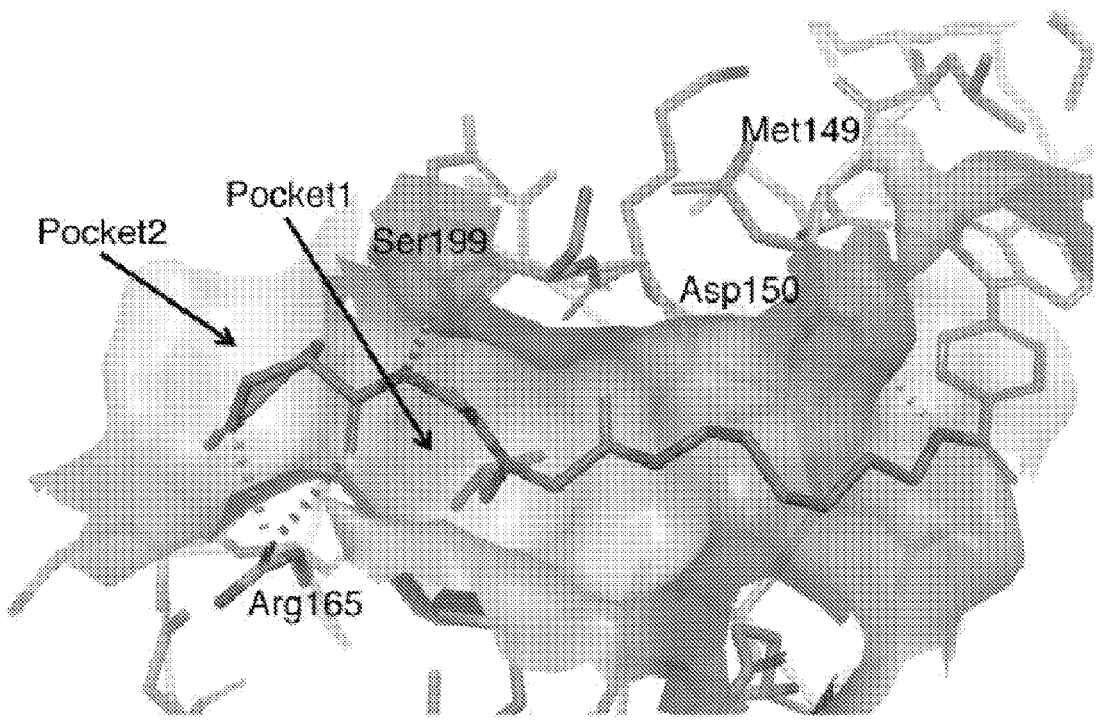

Docking studies of compound 6 with both JNK3 and LRRK2 were performed for compound 6 as a surrogate in order to provide binding modes to guide further optimizations. Thus, compound 6 was docked into the X-ray crystal structure of JNK3 39-402 and the JIP peptide using Glide SP v5.8 (Schrodinger, LLC, NY). FIG. 3A presents the structure of JNK showing the JIP and ATP binding pockets and serves as an orientation and comparison for the modeling of compound 6 presented in FIG. 3B. As shown in FIG. 3B, the indazole-phenyl moiety, Region C, of compound 6 H-bonds to the hinge with the benzamide pointing toward the catalytic loop and the solvent. The docking mode exhibited in FIG. 3B revealed that the tail, Region A, moiety of compound 6 bound to two sub-pockets of the JIP binding site in JNK3, with the N-isobutyl side chain binding to pocket-1 and the chroman ring binding to pocket-2. The two sub-pockets were composed mostly of hydrophobic residues which were responsible for recognizing JIP through a highly conserved $(R/K)(X)_4(L/V)XL$ motif. Sub-pocket-1 bound conserved Leu/Val whereas sub-pocket-2 holds the aliphatic side chain of the Leu/Arg/Lys residues. It is interesting to note that similar hydrophobic interactions occurred between JNK3 and compound 6, although H-bonding interactions were also observed. Thus, this binding motif explains why compound 6 could displace the JIP-peptide with an $IC_{50}$ value of 336 nM (Table 1), despite utilizing binding energy from less than half of the JIP binding sites.

Figure 3C:
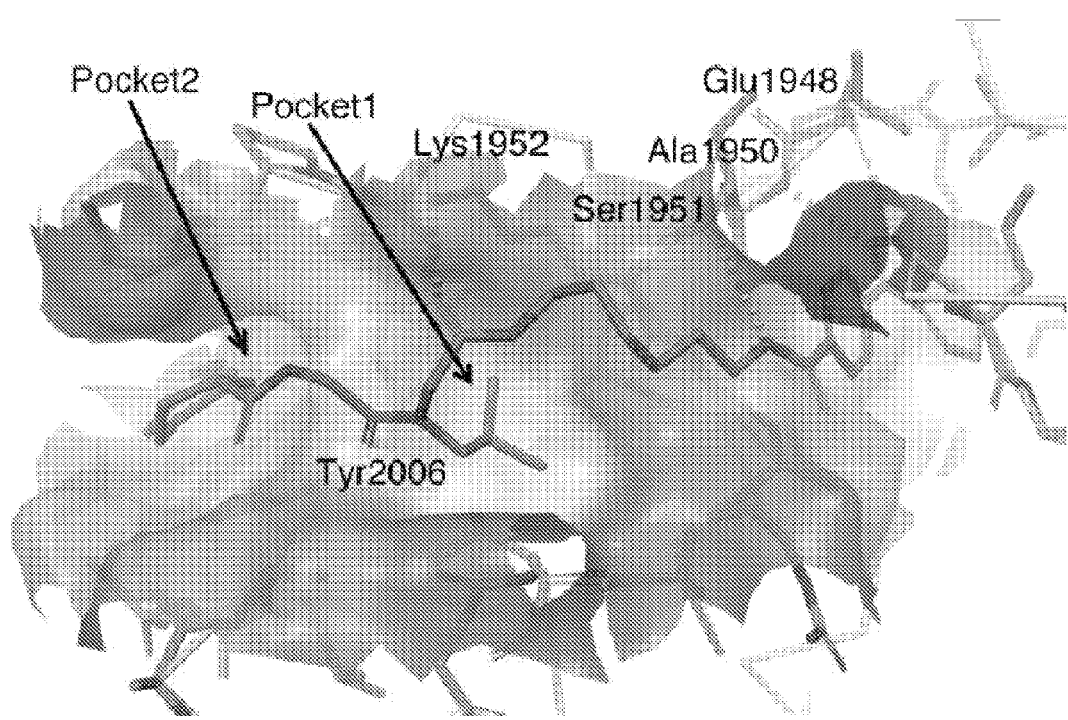

Compound 6 was docked into a homology model of human LRRK2 by using Phyre2, a web based server to model human LRRK2 kinase domain (FIG. 3C). The server produced 20 models with 100% confidence where the sequence alignment between template and query ranged from 22 to 30%. We retrieved six top ranked models and comparison of the models showed an average r.m.s.d. of 1.1 Å over core kinase domains indicating the similarity among the models. We further inspected the models using PyMol to inspect the hinge binding region and the adjacent surface binding pockets. We chose the top ranked model based on the crystal structure of c-Abl Tyrosine Kinase with the PDB ID of 2FO0 (sequence identity of 23% with human LRRK2) for the docking experiment. Importantly, the chosen model structure had hydrophobic pockets similar to the JIP binding site of JNK3. As shown in FIG. 3C, the indazole moiety bound, as expected, to the hinge Region C with H-bond formation. The homology model of human LRRK2 showed similar surface binding pockets to JIP binding sites in JNK3 at the C-lobe near the ATP pocket. Interestingly, the pocket-binding moiety of the inhibitor, Region A, bound to surface pockets in an orientation very similar to that in JNK3. This surface-pocket binding was reinforced by strong hydrophobic interactions of the isobutyl group and the chroman ring in their corresponding binding pockets.

Figure 4:
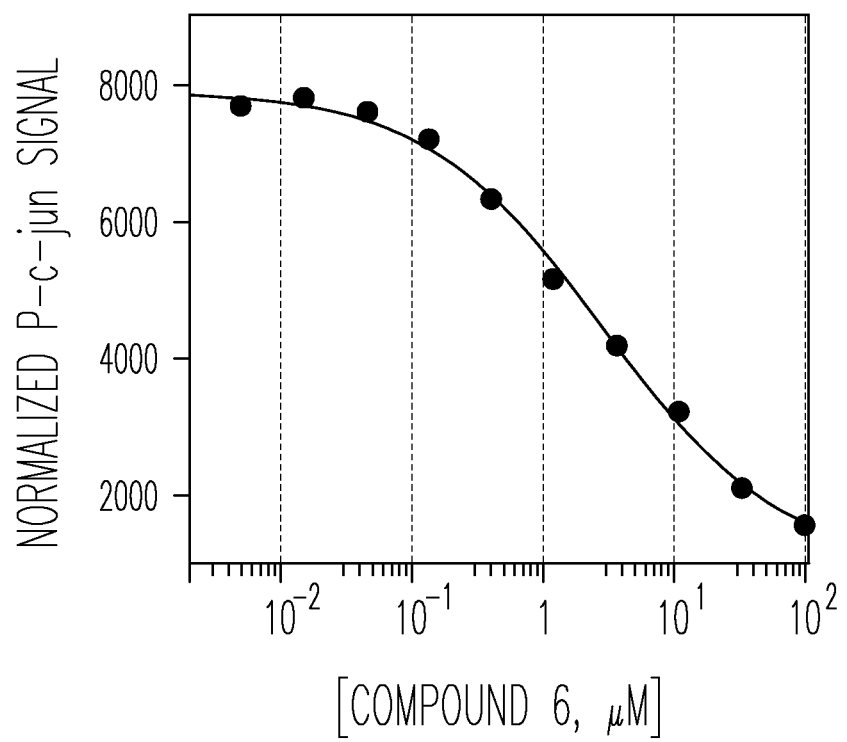
FIG. 4 shows the result of assays to determine the inhibition of the c-jun phosphorylation by compound 6 in H9C2 cardiomyocyte cells. The $IC_{50}$ was calculated to be 2.8±0.5 μM. Standard error is given.
Figure 7:
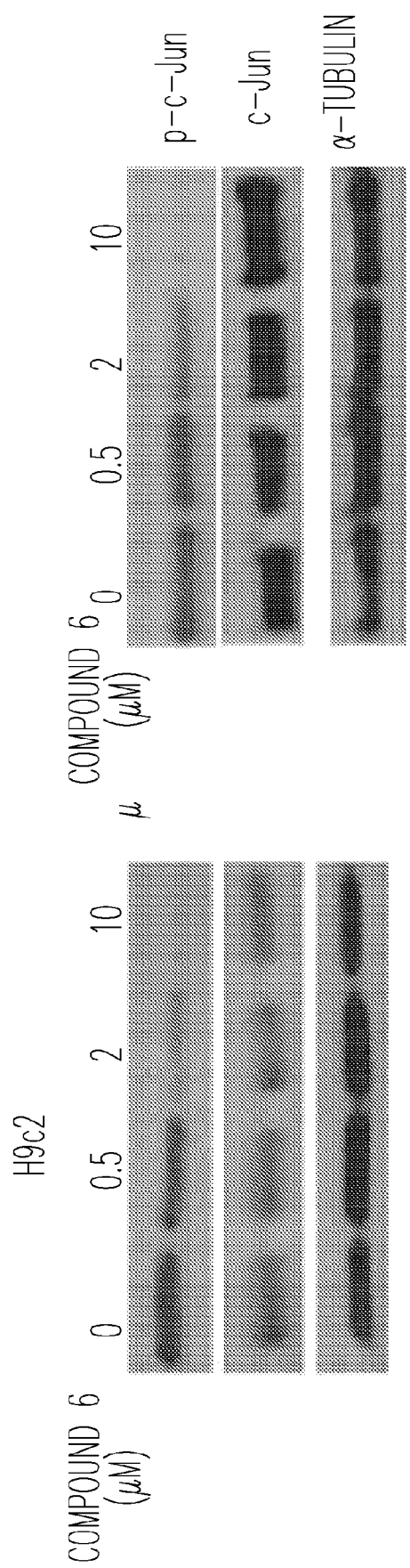
FIG. 7 depicts Western blots showing inhibition of the c-jun phorphorylation by compound 6.

To analyze the cell activity of compound 6 and its analogs an In-cell Western detection assay was set up where phosphorylation of c-Jun was monitored. As seen in FIG. 4, compound 6 began to inhibit the phosphorylation significantly from ~100 nM and its $IC_{50}$ was calculated to be 2.8 µM, indicating that 6 is a cell permeable small molecule inhibitor. This finding was corroborated by Western blot analysis in H9C2 and N2a cells (FIG. 7). Considering the reasonably high biochemical kinase selectivity (coupled with its low µM cell potency), compound 6 is believed to be a good in vitro probe molecule for studying the biology and the signal pathways related to JNK/LRRK2 (and mutant LRRK2s).

Table 2 shows the IC50 data of cell-based assays for JNK bidentate inhibitors (n=4).

TABLE 2

| Cell-Based IC50 for JNK Bidentate Inhibitors (n = 4) | |
|---|---|
| Compound | Cell-based p-c-Jun inhibition (IC50, µM) |
| 5 | 37.4 ± 22.3 |
| 6 | 2.8 ± 0.51 |
| 9 | 80.4 ± 41.4 |
| 10 | 1.4 ± 0.34 |
| 12 | 19.8 ± 7.8 |
| 13 | 9.6 ± 3.0 |

Figure 5A:
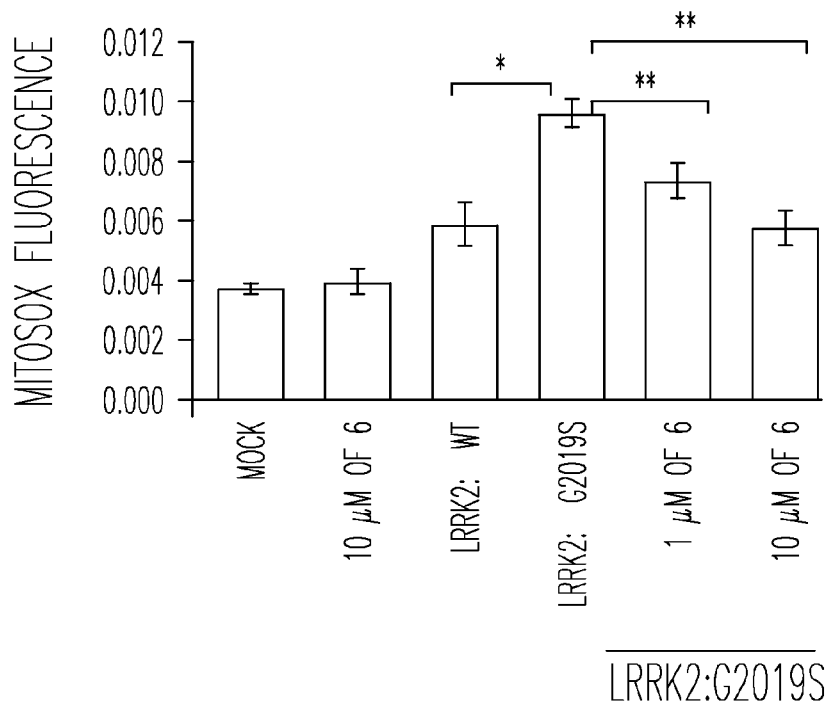
FIGS. 5A, 5B, and 5C, depict the results of assays to determine the protection of LRRK2:G2019S-induced mitochondrial dysfunction and cell death by compound 6. Significance between LRRK2:WT and LRRK2:G2019S are indicated by a single asterisk (p<0.05) (*), while differences between cells expressing LRRK2:G2019S and compound 6 treated cells expressing LRRK2:G2019S are indicated by a double asterisk (p<0.05) (**). Error bars denote standard deviation.
Figure 5B:
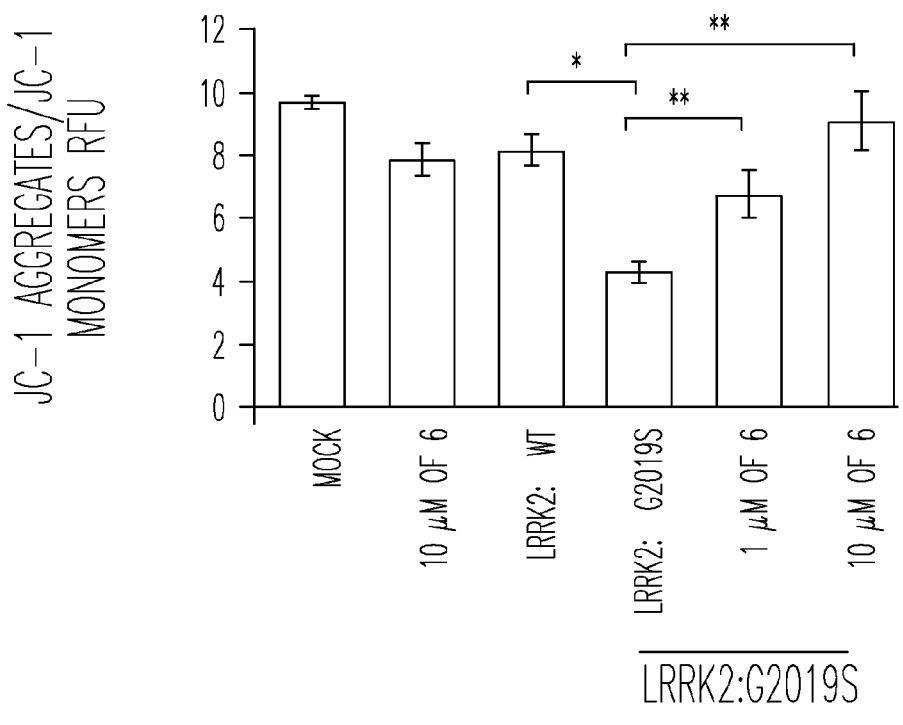
Figure 5C:
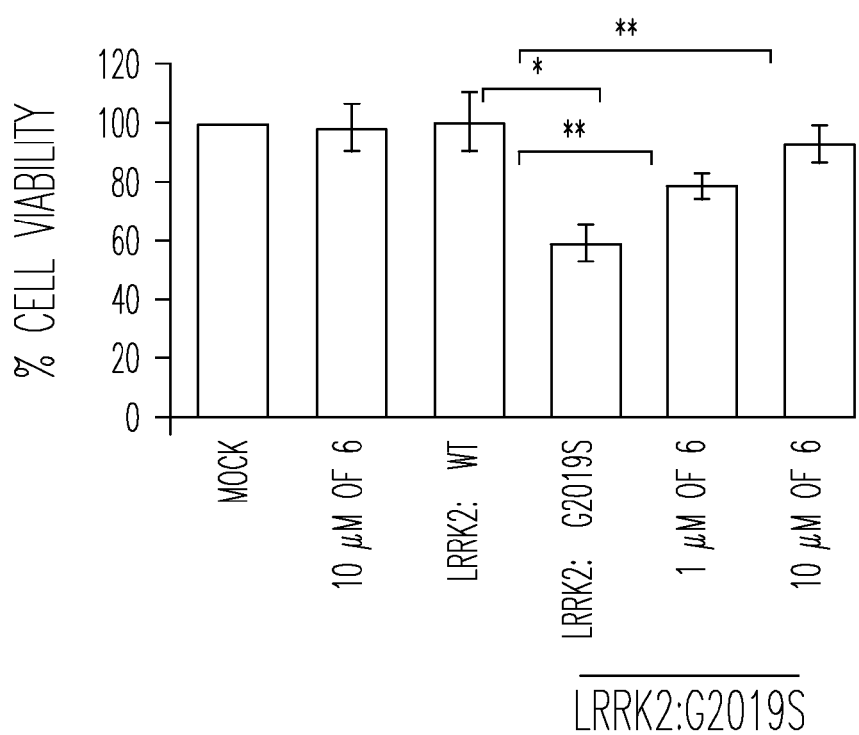

We next tested if compound 6 was potent in cell-based functional assays that measured reactive oxygen species (ROS) generation, mitochondrial membrane potential (MMP), and cell viability. We had previously shown that JNK inhibition had significant effects on all of these mitochondrial functional parameters in HeLa cells. FIG. 5 presents the effects that compound 6 had on all of these measures in the human dopaminergic SHSY5Y cell line. FIG. 5A shows that transfection of SHSY5Y cells with LRRK2: G2019S caused a ~2-fold increase in ROS generated as measured by Mitosox fluorescence. Addition of either 1 µM or 10 µM compound 6 reduced the ROS levels in a statistically significant manner ($p<0.05$). Similarly, compound 6 protected against the LRRK2:G2019S-induced decreases in MMP in a dose dependent manner where 10 µM compound 6 returned MMP dissipation to untreated levels (FIG. 5B). Finally, LRRK2:G2019S-induced cell loss was measured showing ~50% less viable cells (FIG. 5C). In the presence of 10 µM compound 6, cell viability returned to >95% ($p<0.05$). These results indicate that the bidentate dual inhibitor 6 is effective against representative models of LRRK2:G2019S-induced toxicities in human dopaminergic cells.

Figure 6A:
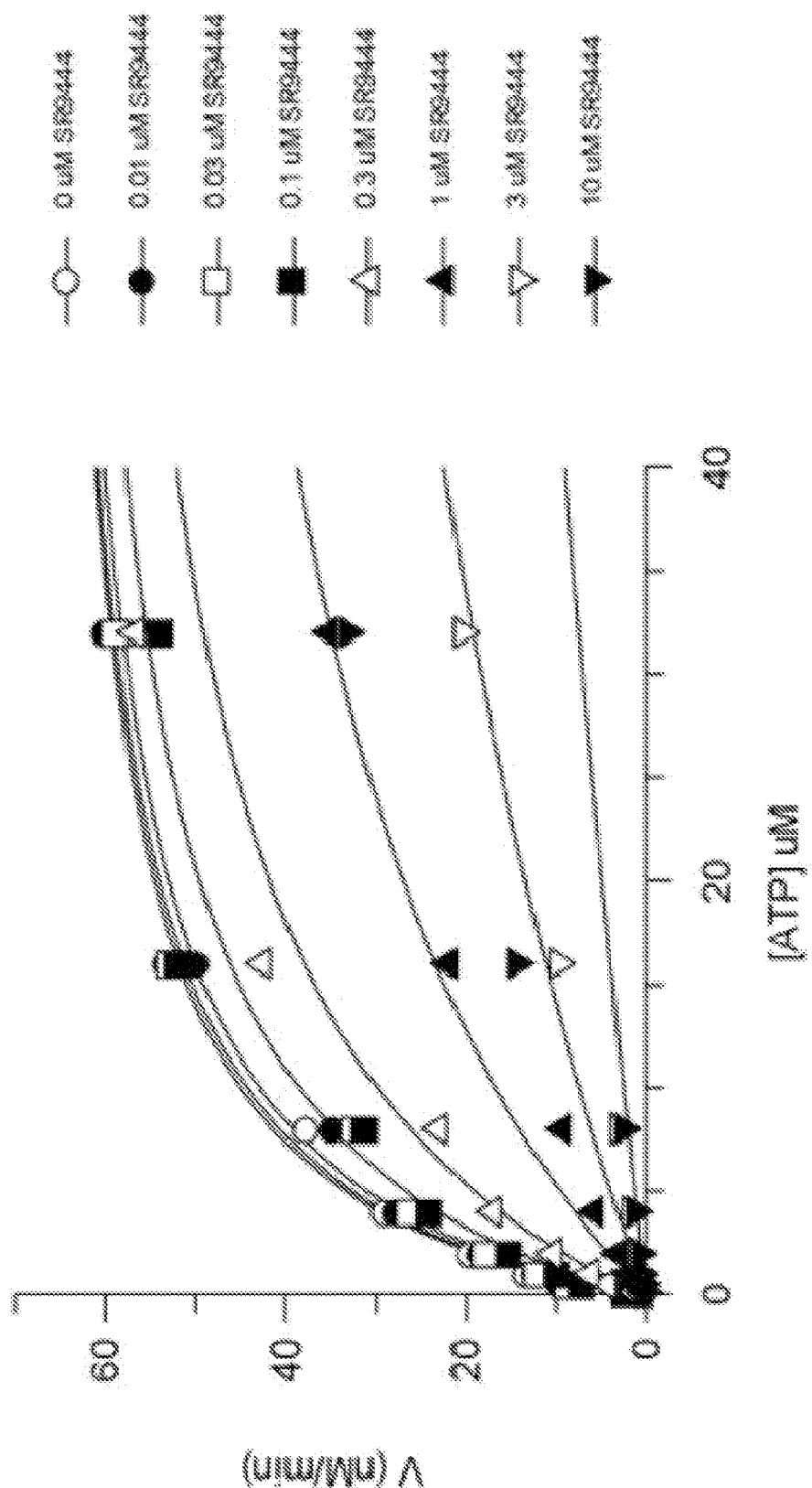
FIG. 6 shows graphic data of ATP competitive binding assays of JNK3α1 with compound 6. (A) Non-linear least squares fitting of the data using an equation for competitive inhibition at eight concentrations of compound 6. (B) Double reciprocal plots and linear regression of the data shown in A.
Figure 6B:
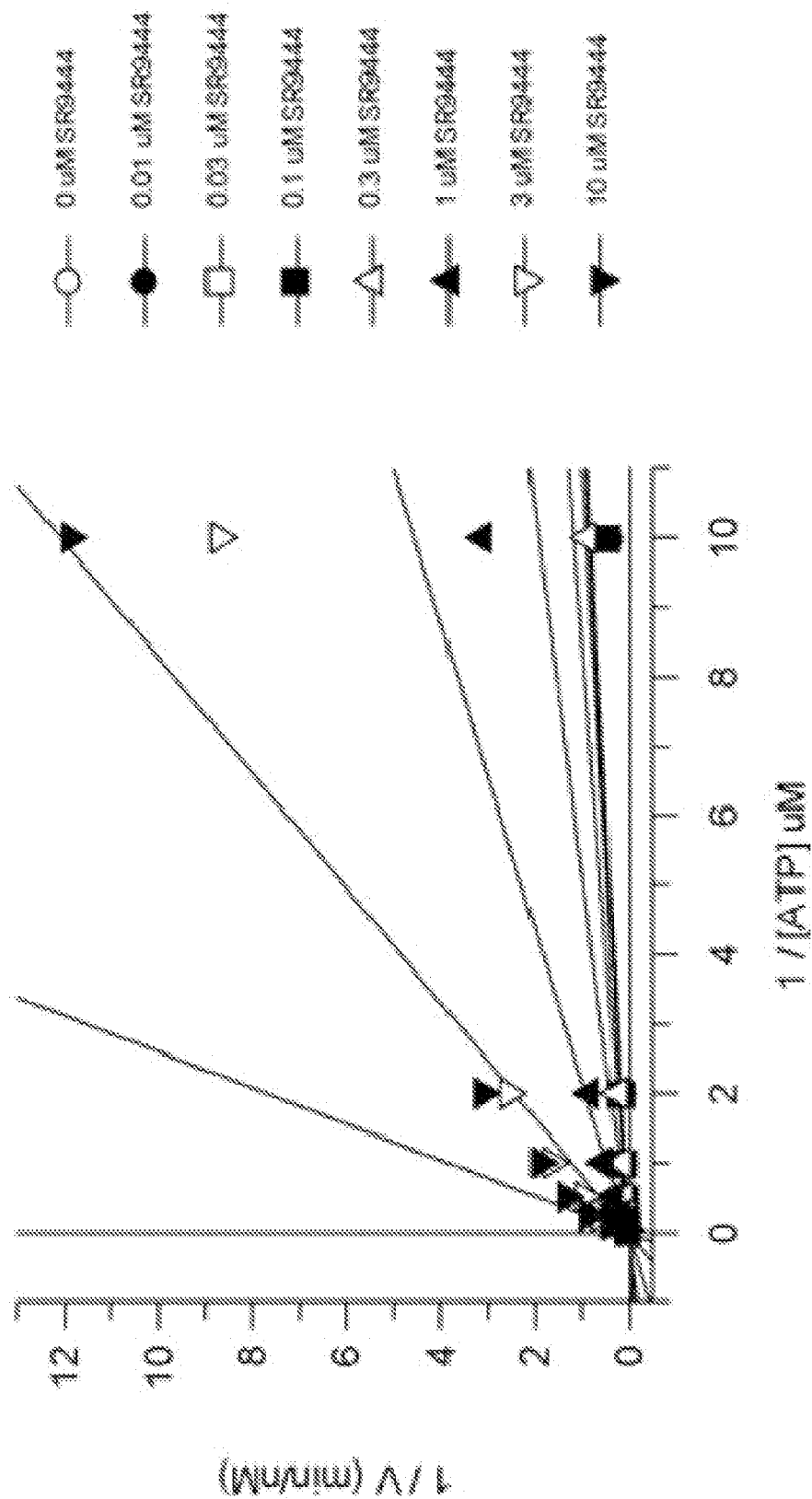

Our initial enzyme inhibition profiling against a panel of 21 representative kinases from several kinase families (JNK3, JNK1, p38α, ROCK1, ROCK2, CDK5, CDK7, CLK1, EGFR, ERK2, FLT1, GSK3α, IKKβ, JAK3, LCK, LIMK1, LRRK2, MKK4, PKA, SGK1, and SYK) at 10 µM inhibitor concentration, revealed that compound 6 inhibited significantly only JNKs (~100%) and LRRK2 (94%), and had moderate inhibition of CLK1 (50%, i.e., $IC_{50}$~10 µM). To augment this we screened an additional 96 kinases at 10 µM in the Ambit binding screen to get a broader sense for the selectivity of this compound. FIG. 6 shows that only six of the 96 kinases tested had greater than 90% binding to 6 at 10 µM. Given the high concentration used in this assay, the data suggest that 6 is a largely selective JNK and LRRK2 kinase inhibitor (~5% of kinases inhibited by 6) and that this selectivity could possibly be attributed to the bidentate binding nature of 6. Since minimal SAR optimizations have been made on this probe molecule it is believed that high selectivity for this class of inhibitors could easily be achieved by exploiting the bidentate binding character of this class.

The strong inhibition of 6 against LRRK2 was a surprise but also a pleasant bonus for our efforts since we hypothesized that dual JNK3 and LRRK2 inhibition may be more efficacious in neuroprotection, especially since both targets have demonstrated benefit in PD models, and a dual inhibitor is what we are searching for. To demonstrate the ability of LRRK2 inhibition, compound 6 was titrated in both wild-type LRRK2 and PD specific mutant LRRK2-G2019S (FIG. 2), and was found to possess an enzyme inhibition activity of $IC_{50}$~100 nM for both of them. High LRRK2 inhibition was also found for most of the bidentate inhibitors with similar structures to that of compound 6 (data not shown), indicating that there is a general dual inhibition pattern for this series.

To establish that substrate competitive JNK inhibitors are protective against ischemia/reperfusion (I/R) injury, the in vitro evaluation of the role of JNK on cardiomyocyte cell death and survival centered on monitoring a number of mitochondrial attributes, such as oxidative stress (ROS), membrane potential, and cell death. To demonstrate that the JNK pathway was activated under $H_2O_2$ stress conditions in H9c2 cardiomyocyte-like cells, we analyzed the time course for JNK and c-jun activation by Western analysis. The levels of JNK immuno-reactivity did not change with treatment of $H_2O_2$ over an 8 hr time course as expected. In contrast, there was only a faint p-JNK signal at t=0 hr (for the 55 kDa isoform) with a time-dependent increase in p-JNK signal beginning at 1 hr showing a maximum at 6 and 8 hr after $H_2O_2$ treatment. These results are consistent with a robust time-dependent activation of JNK in H9c2 cardiomyocyte-like cells after oxidative stress imposed by $H_2O_2$. Like JNK, there was no change in the c-jun immuno-reactivity after treatment with $H_2O_2$. However, a time-dependent increase in p-c-jun immuno-reactivity was seen beginning at 1 hr after $H_2O_2$ treatment peaking between 4-6 hr after treatment. These results also show activation of the JNK pathway, as monitored by the immediate downstream substrate c-jun, following oxidative stress in cardiomyocytes. Immuno-reactivity of α-Tubulin was used as a loading control.

To establish that JNK translocated to the mitochondria and interacted with Sab, and that this interaction could be blocked with a KIM domain designed substrate competitive peptide, the following experiments were carried out: Mitochondria were isolated from H9c2 cells treated for 20 minutes with 100 μM $H_2O_2/FeSO_4$ and Western analysis used to determine if JNK, MKK4, and Sab were localized to the mitochondria. When H9c2 cells were treated with PBS (control) there was no JNK localized to the mitochondria but when treated with 100 μM $H_2O_2/FeSO_4$ the 55 kDa splice variant of JNK was found on the mitochondria. Similarly, a 42 kDa band corresponding to MKK4 (an upstream activator of JNK) was only detected in cells treated with 100 μM $H_2O_2/FeSO_4$ suggesting that MKK4, like JNK, was brought to the mitochondria in H9c2 cells under oxidative stress conditions. The putative JNK mitochondrial scaffold protein Sab was also present on the mitochondria, and COX-IV and SOD1 were present in equal amounts in both samples suggesting equal loading and confirming JNK and MKK4 localization to the mitochondria. Finally, GAPDH immuno-reactivity is shown to indicate no contribution from cytosolic fraction. These data suggest that oxidative stress drives JNK and MKK4 to the mitochondria and this may have a significant role in cardiomyocyte function, survival, and death.

To establish that JNK interacts with Sab and MKK4 on the mitochondria under oxidative stress, we treated H9c2 cells with $H_2O_2/FeSO_4$ and immuno-precipitated the mitochondrial complex with Sab and blotted for Sab, JNK, and MKK4. Western analysis showed that Sab was located on the mitochondrial membrane when no oxidative stress was applied as expected, whereas JNK and MKK4 were not. However, upon treatment of the cells with $H_2O_2/FeSO_4$, JNK and MKK4 were driven to the mitochondria and were associated with Sab. These results suggest that oxidative stress caused JNK and MKK4 to be localized to the mitochondria and that this interaction may be mediated by Sab. Western blot analysis of phospho-JNK and JNK in mitochondrial preps from H9c2 cells showed that JNK and p-JNK were translocated to the mitochondria upon stimulation of H9c2 cells with 100 μM $H_2O_2/FeSO_4$ for 20 min and this translocation was completely blocked by pre-incubation of the cells with 3 μM Tat-Sab peptide. The negative control Tat-Sab scramble peptide had no effect on JNK translocation.

To test whether JNK mitochondrial localization had effects on mitochondrial function we measured the impact of Tat-Sab, and a small molecule JNK inhibitor, SR-3306 (commercially available from Calbiochem), on ROS generation and mitochondrial membrane depolarization in H9c2 cells treated with $H_2O_2$. The ROS fluorescence/cell in the absence of oxidative stress (PBS), was compared to treatment with either 25 μM $H_2O_2$, or 25 μM $H_2O_2$+500 nM SR-3306, or 25 μM $H_2O_2$+3 μM Tat-scramble peptide, or 25 μM $H_2O_2$+3 μM Tat-Sab peptide. The results show that 25 μM $H_2O_2$ increased ROS generation by ~3-fold and the addition of either 500 nM SR-3306 or 3 μM Tat-Sab reduced ROS generation by ~2-fold compared to the 25 μM $H_2O_2$ treatment.

The Tat-scramble peptide had no effect on reducing ROS. A similar effect was seen when mitochondrial membrane potential was measured by Rhodamine 123 detection. These results both suggest that Tat-Sab-mediated inhibition of JNK translocation to the mitochondria decreased ROS generation and mitochondrial membrane potential perturbation despite the oxidative stress-induced environment caused by addition of 25 μM $H_2O_2$. Similarly, both ROS generation and membrane depolarization effects elicited by oxidative stress in H92c cells were blocked by inhibition of JNK with the small molecule, SR-3306 (commercially available from Calbiochem). Finally, the effect of SR-3306 or Tat-Sab on cell viability in response to oxidative stress was measured by a Cell-Titer Glo luminescent assay. H9c2 cells treated with 25 μM $H_2O_2$ were ~40% viable, whereas addition of 500 nM SR-3306 to cells treated with 25 μM $H_2O_2$ increased viability to ~80%, and addition of 3 μM Tat-Sab peptide to cells treated with 25 μM $H_2O_2$ increased viability to ~65% compared to 95% viable in untreated cells. These results suggest that both preventing JNK from translocating to the mitochondria with 3 μM Tat-Sab peptide, or inhibiting JNK activity with 500 nM SR-3306 promoted cell survival in cardiomyocyte-like cells suggesting a critical role for JNK in ROS generation, mitochondrial dysfunction, and cell viability during oxidative stress in vitro.

Cytosolic/nuclear preps showed increased p-JNK and p-c-jun after $H_2O_2/FeSO_4$ treatment but no inhibition of c-jun phosphorylation suggesting that Tat-Sab prevented JNK translocation to the mitochondria but does not inhibit JNK activity.

To demonstrate that the JNK pathway was indeed activated during ischemia/reperfusion, we measured the phospho-c-jun Western blot signal after 30 minutes ischemia and at different time points of reperfusion. Western blot analysis of p-c-jun at different time points of reperfusion showed there was no p-c-jun signal prior to I/R and there was a robust increase in the p-c-jun signal at 30 min after reperfusion, persisting at 1 hr, 2 hr, and 6 hr of reperfusion. The p-c-jun signal was greatly diminished at 24 hr after reperfusion. Tubulin is shown as a loading control. These results indicated that the JNK pathway was activated after I/R and the p-c-jun signal had a time course which was activated early during the reperfusion component of the injury.

After establishing JNK activation during I/R, we demonstrated that ATP competitive JNK inhibitors designed in our lab could be effective in reducing infarct volume in rat hearts. The in vivo efficacy of SR-3306 in anesthetized rats after 30 minutes ischemia and 24 hours reperfusion was evaluated. The results show that the AAR for each of the three groups was approximately the same ranging from 63±2% in the DMSO group to 69±3% in the SR-3306 treated group. The DMSO vehicle treated group showed the infarct size (IS) was 35±3.1% of the AAR. Treatment with 40 mg/kg, 3-aminobenzamide, a positive control for I/R protection, showed the decrease in IS was 26±1.5% of AAR, a statistically significant (p=0.048) effect. Treatment with 5 mg/kg SR-3306 also showed a statistically significant (p<0.05) decrease where IS was 23±3.5% of AAR. These results show that a modest dose of SR-3306 was protective in the I/R MI rat model.

To show that blocking JNK translocation to the mitochondria protects against I/R Injury in vivo we utilized the SabKim1 peptide as a substrate competitive inhibitor. The protection afforded to both the whole heart and the apex of the left ventricle by 2 mg/kg Tat-Sab after I/R injury was evaluated, and showed the whole heart percent infarct for the left ventricle indicating 25.9±3.9% infarct after I/R. Tat-scramble peptide did nothing to reduce the infarct volume while treatment with 2 mg/kg Tat-Sab reduced the infarct volume to 16.1±3.7% (a reduction of 38%, p<0.0001). The protective effect of Tat-Sab is even more profound if only the apex is considered. The apex only percent infarct for the left ventricle was 45.1±6.0% infarct after I/R. Again, Tat-scramble peptide did nothing to reduce the infarct volume while treatment with 2 mg/kg Tat-Sab reduced the infarct volume to 19.9±5.9% (a reduction of 56%, p<0.0001).

To correlate the reduction in infarct volumes afforded by blocking JNK translocation to the mitochondria to measures of oxidative stress, we measured 4-hydroxynonenal (4-HNE; a measure of lipid peroxidation), protein carbonyls, and aconitase activity in the presence and absence of Tat-Sab during I/R. 4-HNE levels were increased 8.8-fold (p<0.05) during I/R compared to sham, and were reduced by 2.5-fold (p<0.05) when I/R happened in the presence of 2 mg/kg Tat-Sab. Similarly protein carbonylation was increased 9.4-fold (p<0.05) during I/R compared to sham, but this change was reduced by 2.6-fold (p<0.05) in the presence of 2 mg/kg Tat-Sab. Finally aconitase activity, a measure of redox activity in the cell, was decreased by 13-fold (p<0.05) during I/R compared to sham, and this was restored to approximately 60% the value of the sham group when I/R happened in the presence of 2 mg/kg Tat-Sab.

Compounds and Compositions

The invention is directed, in various embodiments, to bidentate kinase inhibitor compounds of formula (I) wherein

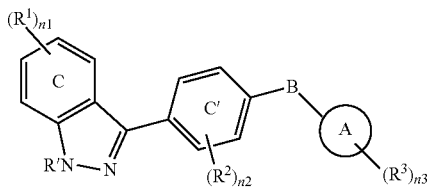

each of ring C and ring C' independently comprises 0, 1, 2, or 3 nitrogen atoms therein; or ring C' is absent, and a direct bond or an ethynyl group bonds ring system C to group B;

group A is a 3-16 membered saturated, partially unsaturated, or aromatic, mono-, bi-, or tricyclic ring system, comprising 0-8 heteroatoms selected from the group consisting of O, N, and $S(O)_q$ wherein q=0, 1, or 2, substituted with n3 $R^3$ groups;

$R^1$, $R^2$, and $R^3$ are each independently at each occurrence OR, $NR_2$, CN, $CF_3$, halo, or a $(C_{1-6})$alkyl optionally comprising therein any of NR', $S(O)_q$, O, C(=S), C(=O), C(=O)O, OC(=O)O, C(=O)C(=O), C(=O)NR', O(C=O)NR' NR'C(=O)NR', SO2NR', or C(=O)NR'NR'; or $R^1$, $R^2$, and $R^3$ are each independently a 3-16 membered saturated, partially unsaturated, or aromatic, mono-, bi-, or tricyclic ring system, comprising 0-8 heteroatoms selected from the group consisting of O, N, and $S(O)_q$ wherein q=0, 1, or 2, substituted with n4 $R^4$ groups;

$R^4$ is independently at each occurrence OR, $NR_2$, CN, $CF_3$, halo, or a $(C_{1-6})$alkyl optionally comprising therewithin any of NR', $S(O)_q$, O, C(=S), C(=O), C(=O)O, OC(=O) O, C(=O)C(=O), C(=O)NR', O(C=O)NR' NR'C(=O) NR', SO2NR', or C(=O)NR'NR';

n1=0, 1, 2, or 3; n2=0, 1, 2, or 3; n3=0, 1, 2, 3, 4, or 5; n4=0, 1, 2, 3, 4, or 5;

R is H, $(C_{1-6})$alkyl, or $(C_{1-6})$acyl;

R' is H, $(C_{1-6})$alkyl, or $(C_{1-6})$acyl; or R' is a 5-16 membered saturated, partially unsaturated, or aromatic, mono-, bi-, or tricyclic ring system, comprising 0-8 heteroatoms selected from the group consisting of O, N, and $S(O)_q$ wherein q=0, 1, or 2, substituted with n4 $R^4$ groups;

B is a linker comprising at least 8 backbone atoms selected from C, N, O, and S(O)q, wherein the linker can be linear or can comprise 1-4 cycloalkyl, heterocyclyl, aryl, or heteroaryl ring systems, any of which is optionally mono- or independently multi-substituted with R';

or a pharmaceutically acceptable salt thereof, or a hydrate, solvate, or prodrug thereof.

For example, for compound of formula (I), A can be any one of:

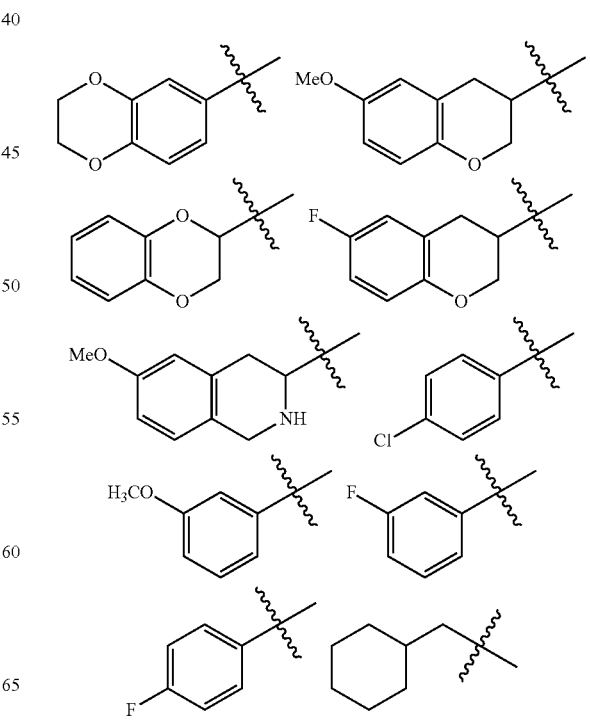

-continued
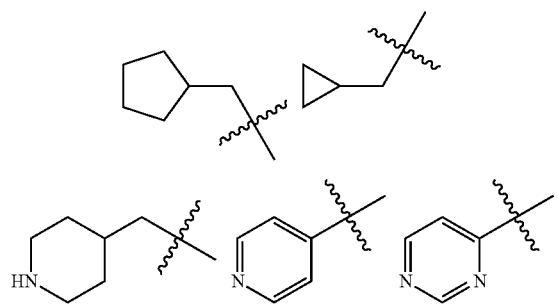
wherein a wavy line indicates a point of bonding.
More specifically, A can be
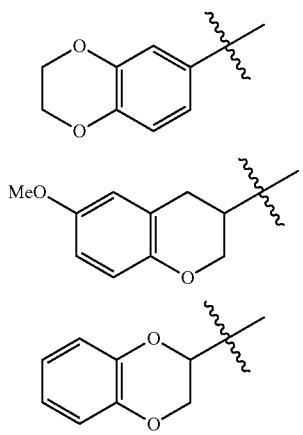
wherein a wavy line indicates a point of bonding.
For example, B can be any one of:
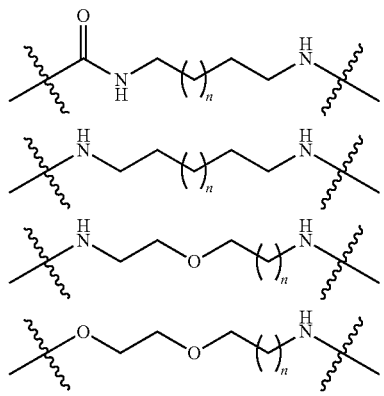
wherein n is 2 to about 14, or is
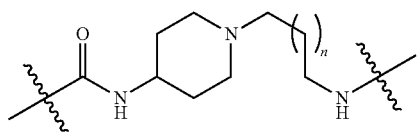
-continued
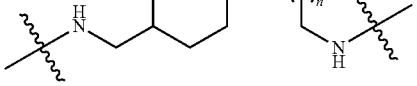
wherein n is about 2 to about 14, or is
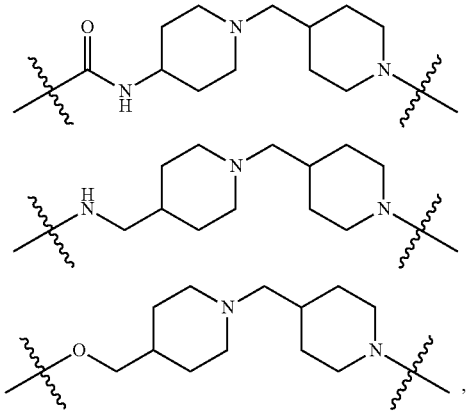
wherein the wavy lines indicate points of bonding to groups A and C, in either orientation.
More specifically, B can be any one of:
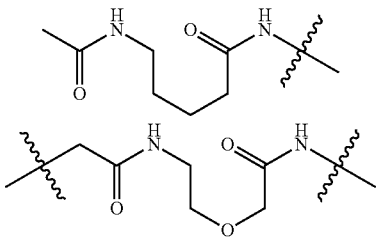

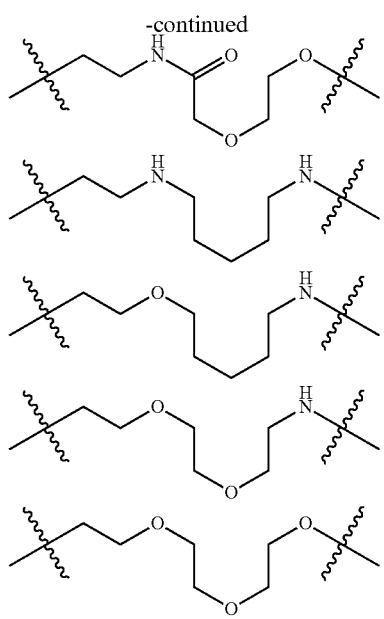
wherein the wavy lines indicate points of bonding to groups A and C, in either orientation.
For example, groups C/C' can be any one of the following:
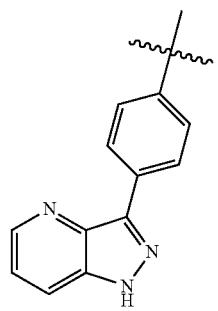
Y
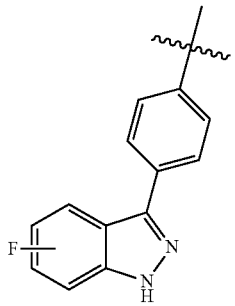
X
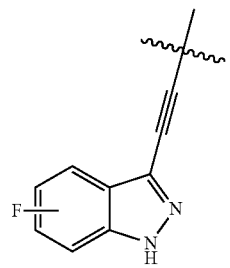
Z
wherein a wavy line indicates a point of bonding.
More specifically, the compound of formula (I) can be any one of the following:
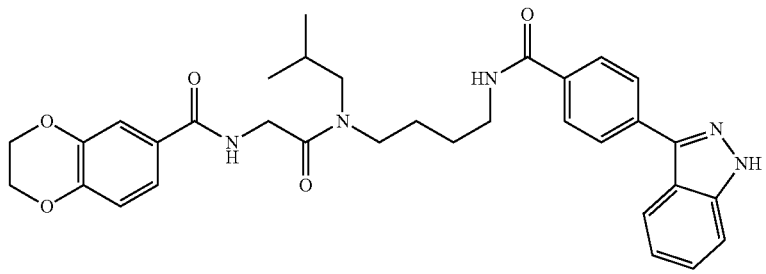
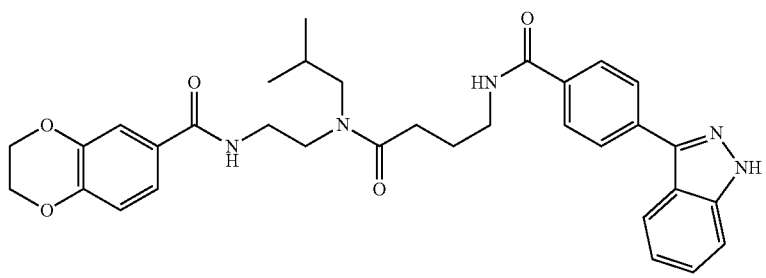

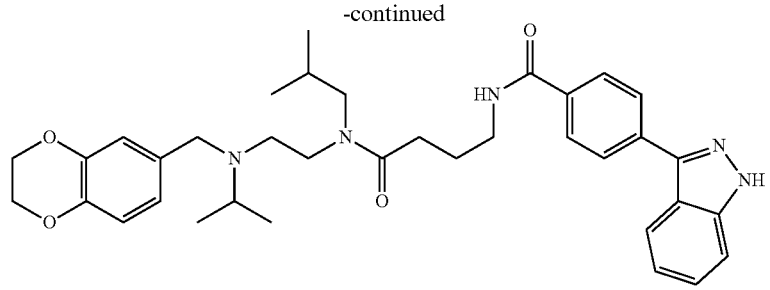
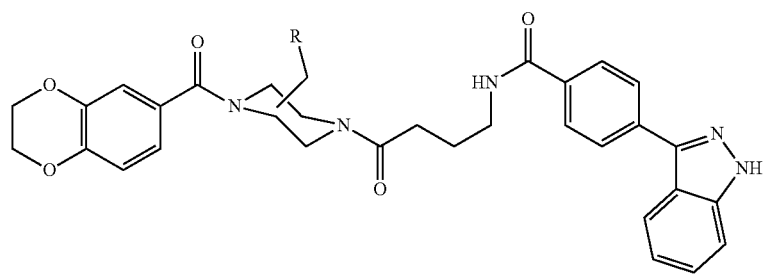
More specifically, the compound of formula (I) can be any one of:
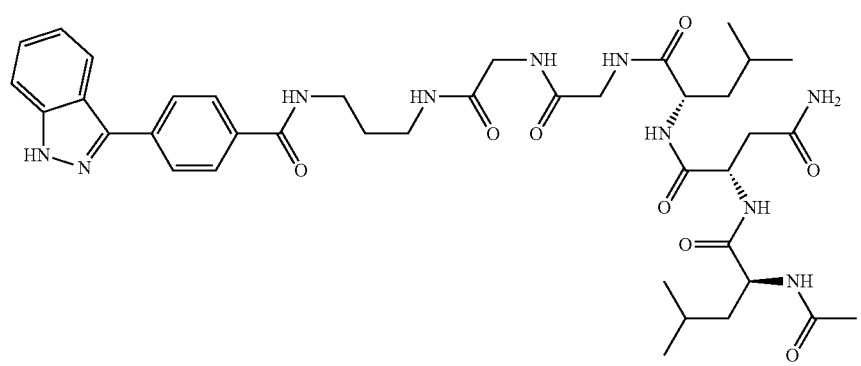
1
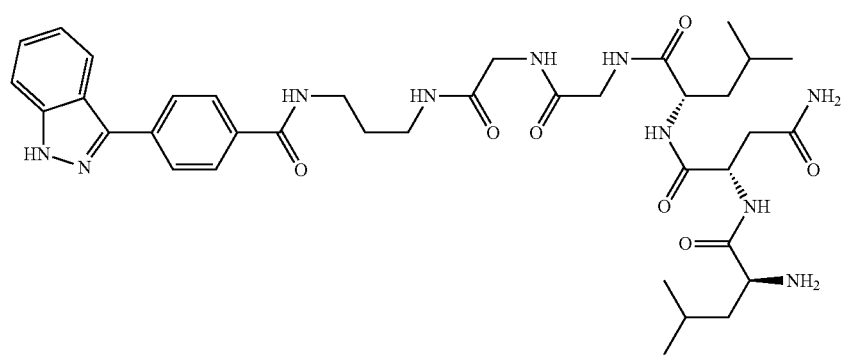
2

-continued
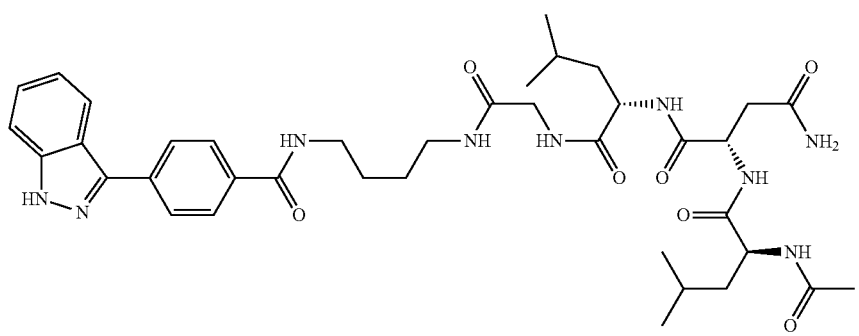
3
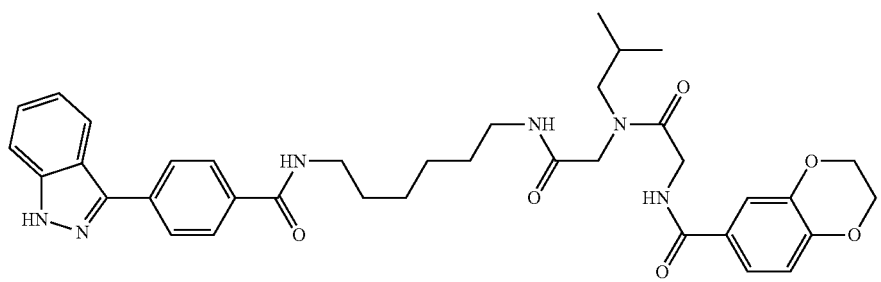
4
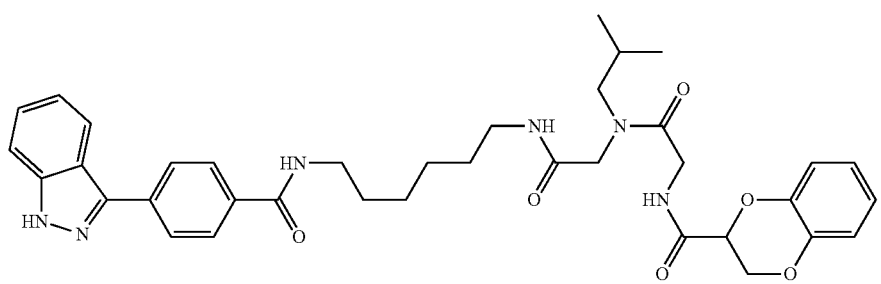
5
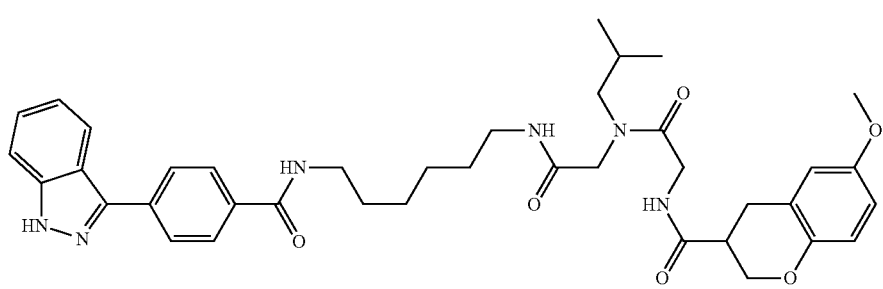
6
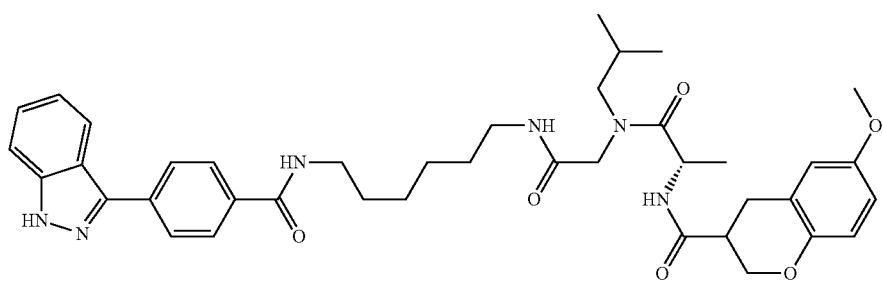
7

-continued

8

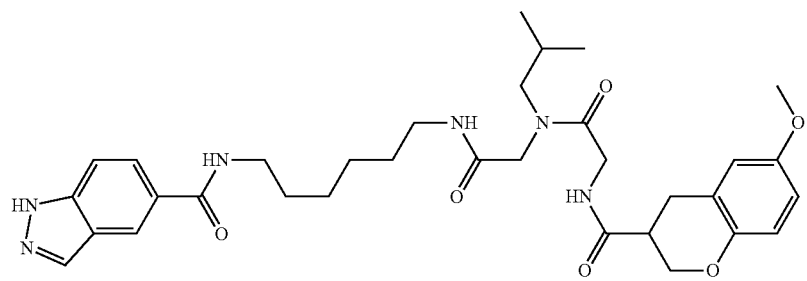

9

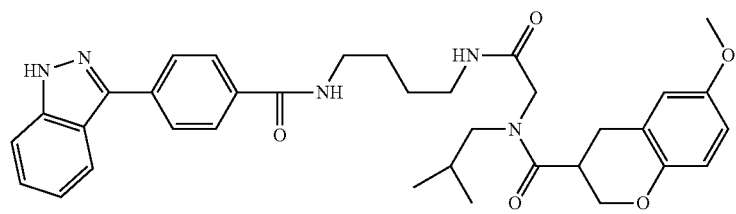

10

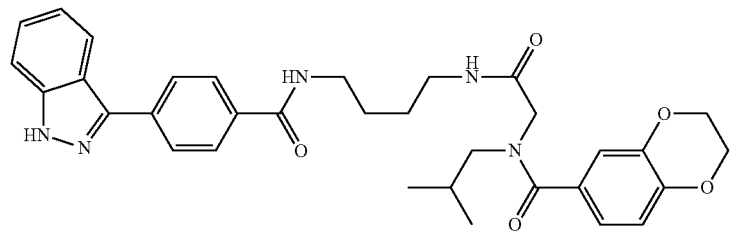

11

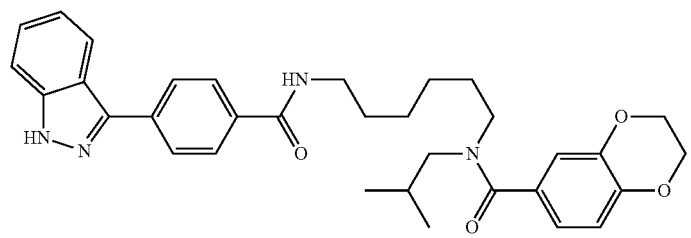

12

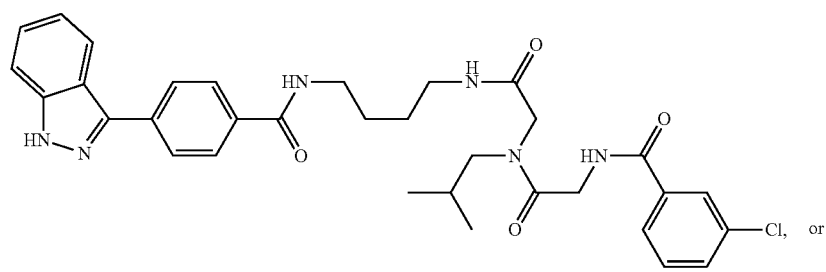

, or

13

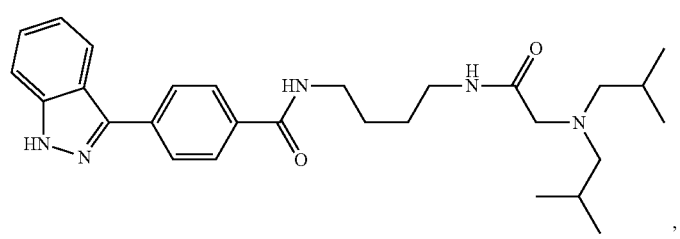

, or a pharmaceutically acceptable salt thereof, or a hydrate, solvate, or prodrug thereof.

Compound 10 (see Scheme 1(A)) was used as a structural lead to explore the structure space for bioactivity of the bidentate kinase inhibitors versus JNK isoforms and against LRRK2. This compound is a potent inhibitor of JNK activity (65 nM) with reasonable cell potency (~1 μM). In addition, it possesses a JIP activity (<400 nM) which we believe is good enough to render high kinase selectivity. Indeed, compound 10 inhibited only LRRK2 ($IC_{50}$=80 nM) in the profiling against 18 representative kinases from a broad spectrum of the kinome at 10 µM. Therefore, compound 10 was judged to be a suitable lead for optimization of good candidates for treatment of MI and other conditions in which these kinases are implicated, including PD.

In the design of these bidendate JNK inhibitors such as compounds 6 and 10, the indazole-phenyl moiety was used to act as an ATP competitive binder, the benzodioxane-isobutyl amide part was used to mimic the binding of the tri-peptide Leu-Asn-Leu in the JIP peptide and (Leu-Asp-Leu in Sab), and the linear chain between them was used as a linker to connect these two key binding moieties. Based on this model, the key for optimization is to discover structural moieties that can strongly bind to the pockets occupied by the Leu-Asn-Leu tri-peptide, and to find appropriate linkers with minimal length (and appropriate orientation) without affecting the binding contributions of both the indazole group and the tri-peptide mimetics.

Scheme 1(B), above, schematically shows the bidentate structure of compound 6, showing the hinge-binding indazole-phenyl, the linker shown as B in formula (I), and the pocket-binding ring system shown as group A in formula (I). A combination of traditional medicinal chemistry and structure-based drug design is applied to optimize these JNK3 inhibitors. The regions of the bidentate kinase inhibitors include: A) The surface pocket binding region moiety (Region A, shown at bottom): since this part is used to mimic the tri-peptide binding of the JIP peptide, structural modification of it is critical for both potency and kinase selectivity, and it can also affect other pharmaceutical properties such as solubility, cell permeation, DMPK etc; B) The linear linker moiety: structural modifications in this region affect the JNK3 activity since its length and conformation determine how well moieties A and C bind to their pockets. Moreover, the properties of this linker can also affect the kinase selectivity since part of it interacts with the JIP binding pocket. Finally, modifications to the ATP competitive (hinge region) binder (Region C) are performed primarily to improve the DMPK properties since an unsubstituted indazole ring might be prone to metabolic oxidations. Based on the proposed binding model, our optimizations primarily focus on Regions A (pocket-binding) and B (linker). Scheme 1(C) shows partial structures that can be used for the pocket-binding (Region A) moiety of a bidentate kinase inhibitor of the invention. These structures include the group A of formula (I), above, plus a portion of the linker B (Region B) to indicate the manner of bonding of the groups A and B in formula (I).

The benzadioxane ring can be replaced by a variety of substituted phenyl rings (A-1 to A-6, Scheme 1(C)). The isobutyl group can be replaced by different alkyl moieties to obtain optimal binding to the pocket originally occupied by one of the Leu residue in the JIP peptide. Building groups A-10 to A-12 contain cyclic rings which can render stronger hydrophobic interactions compared to a simple alkyl group. The pyrrole in A-12 can be used to test whether a group with hydrogen bonding capability is tolerated or even benefits the binding. In addition, the polar group in A-12 can improve the solubility. The 6-carboxylbenzadioxane ring in compound 10 can be reversed and various 3-carboxylbenzadioxane, 3-carboxylchromane, and 3-carboxyltetrahydro-isoquinoline moieties can be used to see whether stronger binding will be obtained (A-13 to A-17). Another reason to apply these groups is that they can improve the aqueous solubility. The positioning of the amide group and the N-alkylation group can be switched, such as in building blocks A-18 to A-23. Finally, a tertiary amine will be used to replace the tertiary amide in SR-9402 (A-24 to A-29). The application of these groups can determine whether an amide carbonyl moiety is critical for effective JNK inhibition and JIP displacement. A variety of tertiary amines can be examined including building blocks containing bis-alkyl substitutions (A-29), bis-benzylic substitutions (A-28), and mixed alkyl-benzylic substitutions (A-24 to A-27).

Several strategies can be used to optimize the linker, Region B (see Scheme 1(D), above). For example, a retro-inverso method can be applied to either the benzamide (B-1, B-2) or the Gly amide (B-3), or to both (B-4). In addition, the benzamide moiety can be replaced by a simple secondary amine (B-5, B-6) or an oxygen either (B-7, B-8), or both the benzamide and the Gly amide can be replaced by a secondary or an ether linkage (B-9 to B-12). These kinds of structural changes can help discover whether a critical H-bonding interaction is involved in the JNK3 inhibition and/or the JIP displacement. The removal of the carbonyl oxygen can also help reduce the molecular weight. Moreover, reduction of the amide NH count can help the compound cell activity. During this optimization, the whole chain length can be increased or reduced (e.g., plus/minus one atom) to get optimal activity.

Another strategy to optimize Region B is to combine the optimization of the linker with that of the isobutyl group in Region A. As shown in Analog-1 of Scheme 1(E), the isobutyl group can be moved from the benzadioxane amide nitrogen to the Gly amide nitrogen. Then both the optimization information from Schemes 1(C) and 1(D) can be applied to optimize Analog-1. For example, Analog-2 is the retro-inverso counterpart to Analog-1, and Analog-3 is tertiary amine structure of Analog-2. The benzamide moiety on the indazole-phenyl group can also be replaced by a secondary amine or an oxygen ether linkage, and the chain length can be varied to obtain optimal binding to JNK isoforms and to LRRK2.

In medicinal chemistry optimizations, reduction of structural flexibility can enhance compound binding and/or increase cell membrane penetration capability. This strategy can also be used for the optimization of Region B. For example, Analog-4 is a ring fused structure of Analog-2. The piperazine ring itself can partly pick up the interaction energy by the isobutyl group, and an alkyl substitution to either the 2- or the 3-position of the piperazine ring can mimic completely the isobutyl group in compound 10. The optimization strategies shown in Schemes 1(C) and 1(D) can be used to refine the structure.

Other options for Region B in bidentate kinase inhibitors of the invention include the following linkers, designated as group B in formula (I), above, can be any one of:

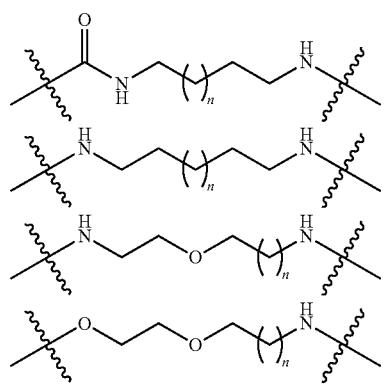

wherein n is 2 to about 14, or is

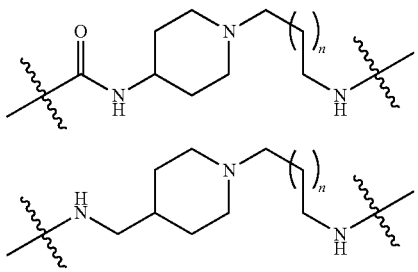

wherein n is about 2 to about 14, or is

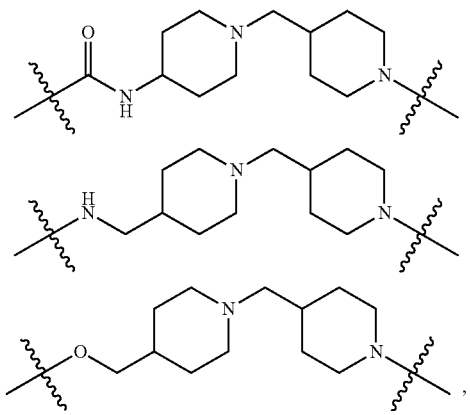

wherein the wavy lines indicate points of bonding to Regions A and C, in either possible orientation. By bonding to Regions A and C (groups A and C of formula (I)), in either orientation is meant that the linker can be present in the bidentate kinase inhibitor compound of formula (I) with either end bonded to group A and the opposite end bonded to group C.

Specific examples of linker B can be any of the following groups:

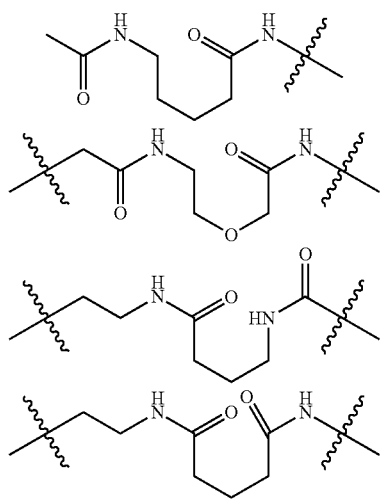

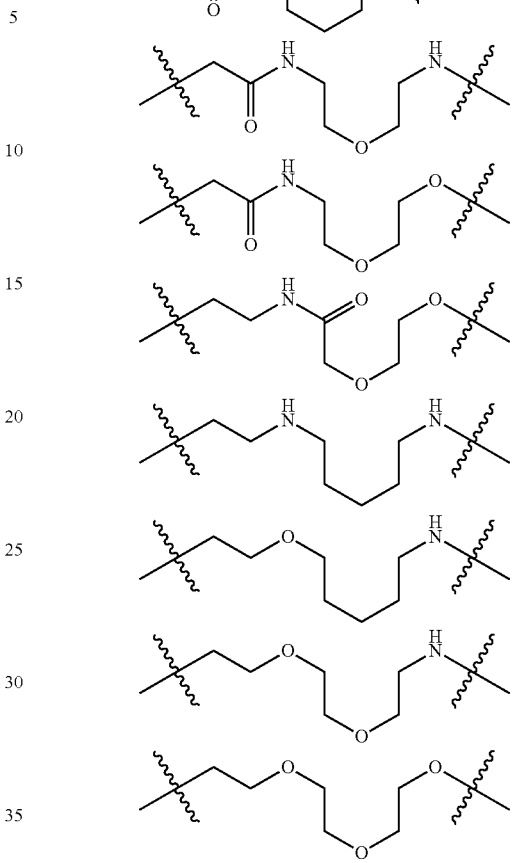

wherein the wavy lines indicate points of bonding to groups A and C, in either orientation.

Region C can be optimized by use of several good JNK hinge binding groups reported in the literature, wherein structures related to the indazole-based structure of compounds 6 and 10 are effective for ATP competitive binding of bidentate JNK inhibitors. The unsubstituted indazole moiety is known to be sensitive to metabolic oxidations, so a fluoro substitution can be used to overcome this problem (compound X) as shown in Scheme 1(F). Application of a corresponding aza-indazole (structure Y) can also be a solution to this problem. In addition, ring C' can be absent, and an ethynyl group can be present, as in structure Z, or ring system C can be directly bonded to linker B.

Table 2, above, presents the inhibition of c-Jun phosphorylation in H9c2 cells for six JNK bidentate inhibitors, compounds 5, 6, 9, 10, 12, and 13. The results show that compounds had cell-based $IC_{50}$s near 1 µM suggesting that these bidentate inhibitors were cell permeable, could inhibit JNK in vitro, and were good candidates for further SAR development.

Definitions

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

All percent compositions are given as weight-percentages, unless otherwise stated.

As used herein, "individual" (as in the subject of the treatment) or "patient" means both mammals and non-mammals. Mammals include, for example, humans; non-human primates, e.g. apes and monkeys; and non-primates, e.g. dogs, cats, cattle, horses, sheep, and goats. Non-mammals include, for example, fish and birds.

The term "disease" or "disorder" or "malcondition" are used interchangeably, and are used to refer to diseases or conditions wherein JNK/LRRK2 plays a role in the biochemical mechanisms involved in the disease or malcondition or symptom(s) thereof such that a therapeutically beneficial effect can be achieved by acting on a kinase, specifically by acting to inhibit the bioactivity of an isoform of JNK such as JNK1, 2, or 3, or on LRRK2. "Acting on" JNK/LRRK2, or "modulating" JNK/LRRK2, can include binding to JNK/LRRK2 and/or inhibiting the bioactivity of JNK/LRRK2 and/or allosterically regulating the bioactivity of JNK/LRRK2 in vivo.

The expression "effective amount", when used to describe therapy to an individual suffering from a disorder, refers to the amount of a compound of the invention that is effective to inhibit or otherwise act on JNK/LRRK2 in the individual's tissues wherein JNK/LRRK2 involved in the disorder is active, wherein such inhibition or other action occurs to an extent sufficient to produce a beneficial therapeutic effect.

"Treating" or "treatment" within the meaning herein refers to an alleviation of symptoms associated with a disorder or disease, or inhibition of further progression or worsening of those symptoms, or prevention or prophylaxis of the disease or disorder, or curing the disease or disorder. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result. A therapeutically effective amount is also one in which any toxic or detrimental effects of compounds of the invention are outweighed by the therapeutically beneficial effects.

Phrases such as "under conditions suitable to provide" or "under conditions sufficient to yield" or the like, in the context of methods of synthesis, as used herein refers to reaction conditions, such as time, temperature, solvent, reactant concentrations, and the like, that are within ordinary skill for an experimenter to vary, that provide a useful quantity or yield of a reaction product. It is not necessary that the desired reaction product be the only reaction product or that the starting materials be entirely consumed, provided the desired reaction product can be isolated or otherwise further used.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

All chiral, diastereomeric, racemic forms of a structure are intended, unless a particular stereochemistry or isomeric form is specifically indicated. In several instances though an individual stereoisomer is described among specifically claimed compounds, the stereochemical designation does not imply that alternate isomeric forms are less preferred, undesired, or not claimed. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

As used herein, the terms "stable compound" and "stable structure" are meant to indicate a compound that is sufficiently robust to survive isolation to a useful degree of purity from a reaction mixture, and formulation into an efficacious therapeutic agent. Only stable compounds are contemplated herein.

When a group is recited, wherein the group can be present in more than a single orientation within a structure resulting in more than single molecular structure, e.g., a carboxamide group C(=O)NR, it is understood that the group can be present in any possible orientation, e.g., X—C(=O)N(R)—Y or X—N(R)C(=O)—Y, unless the context clearly limits the orientation of the group within the molecular structure.

Substituent groups can be categorized into a variety of sets based upon their steric and electronic properties, allowing predictions to be made about the properties of molecules or of domains of molecules incorporating these groups.

For example, steric classifications, i.e., groups that can influence the reactivity of moieties and molecules containing them, include a "sterically bulky" group, that can "sterically hinder" a region or reactive grouping of a molecule. A sterically bulky group is a group of large molecular volume that can block approach of reactants to itself or neighboring groups; an example is a tert-butyl group, wherein the three methyl groups bonded to the central carbon atom serve to impede approach of, e.g., an incoming nucleophile to an adjacent carbonyl group, reducing reaction rate for nucleophilic substitution at that center.

Classifications can be made on the basis of electronic properties as well, that is, where factors such as electronegativity or electropositivity, or resonance factors, enable a substituent group to influence the reactivity of neighboring atoms or groupings of atoms.

For example, an electron-withdrawing group, as is well-known in the art, is a substituent, such as on an aryl ring (e.g., a phenyl ring) that is electronegative and withdraws electron density from an adjacent atom or configuration of atoms. An example is a halo group, such as fluoro, chloro, etc. Another example is a alkylsulfonyl or arylsulfonyl group. These two examples can function to withdraw electron density along a σ, or single, bond, reducing electron densities, e.g., of aryl rings to which they are bonded, consequently reducing the rate and/or favorable energetics of electrophilic substitution of that aryl group. Electron-withdrawing groups can operate through π, i.e., double-bonded (or triple-bonded), systems, where electron density flows via conjugated π bond systems. An example is an α,β-unsaturated enone group, such as an acryloyl group. The carbon-carbon double bond of the enone can act to transmit the polarization of the carbonyl group to, e.g., an aryl ring, withdrawing electron density from the ring.

For example, an electron donating group, as is well-known in the art, is a substituent, such as on an aryl ring (e.g., a phenyl ring) that is electronpositive and donates electron density from an adjacent atom or configuration of atoms. An example is a trialkylsilyl group, where due to the electropositivity of the silicon atom, electron density is pushed onto adjacent atoms or groupings of atoms via a σ, or single, bond. Or, electron donating groups can act via π, i.e., double (or triple) bonds as well. For example, an alkoxyl group, when bonded to an aryl ring, can be electron-donating despite the electronegativity of the oxygen atom, because of electron density donation via π-conjugation into an aryl ring, thus increasing the rate and favorable energetics of electrophilic substitution of the ring.

Groups can also be classified on the basis of polarity (or hydrophilicity) and non-polarity (or lipophilicity). These properties can influence the manner in which molecules can interact via non-bonding interactions with other molecules in the vicinity, such as solvent molecules (polar groups favor dissolution of the molecule in polar solvents like water, alcohol, and the like, and non-polar groups favor dissolution of the molecule in non-polar solvents like hydrocarbons, halocarbons, and the like), and in complex binding interactions, e.g., of small molecules with proteins or other biomolecules, including receptors, enzymes, and the like. Small molecules are believed to interact in a highly specific way with biomolecules such as receptors through "lock and key" type interactions based on steric and electronic factors of the small molecule (ligand) being complementary to the biomolecule (receptor).

When a group, e.g., an "alkyl" group, is referred to without any limitation on the number of atoms in the group, it is understood that the claim is definite and limited with respect the size of the alkyl group, both by definition; i.e., the size (the number of carbon atoms) possessed by a group such as an alkyl group is a finite number, less than the total number of carbon atoms in the universe and bounded by the understanding of the person of ordinary skill as to the size of the group as being reasonable for a molecular entity; and by functionality, i.e., the size of the group such as the alkyl group is bounded by the functional properties the group bestows on a molecule containing the group such as solubility in aqueous or organic liquid media. Therefore, a claim reciting an "alkyl" or other chemical group or moiety is definite and bounded, as the number of atoms in the group cannot be infinite.

The inclusion of an isotopic form of one or more atoms in a molecule that is different from the naturally occurring isotopic distribution of the atom in nature is referred to as an "isotopically labeled form" of the molecule. All isotopic forms of atoms are included as options in the composition of any molecule, unless a specific isotopic form of an atom is indicated. For example, any hydrogen atom or set thereof in a molecule can be any of the isotopic forms of hydrogen, i.e., protium ($^1$H), deuterium ($^2$H), or tritium ($^3$H) in any combination. Similarly, any carbon atom or set thereof in a molecule can be any of the isotopic form of carbons, such as $^{11}$C, $^{12}$C, $^{13}$C, or $^{14}$C, or any nitrogen atom or set thereof in a molecule can be any of the isotopic forms of nitrogen, such as $^{13}$N, $^{14}$N, or $^{15}$N. A molecule can include any combination of isotopic forms in the component atoms making up the molecule, the isotopic form of every atom forming the molecule being independently selected. In a multi-molecular sample of a compound, not every individual molecule necessarily has the same isotopic composition. For example, a sample of a compound can include molecules containing various different isotopic compositions, such as in a tritium or $^{14}$C radiolabeled sample where only some fraction of the set of molecules making up the macroscopic sample contains a radioactive atom. It is also understood that many elements that are not artificially isotopically enriched themselves are mixtures of naturally occurring isotopic forms, such as $^{14}$N and $^{15}$N, $^{32}$S and $^{34}$S, and so forth. A molecule as recited herein is defined as including isotopic forms of all its constituent elements at each position in the molecule. As is well known in the art, isotopically labeled compounds can be prepared by the usual methods of chemical synthesis, except substituting an isotopically labeled precursor molecule. The isotopes, radiolabeled or stable, can be obtained by any method known in the art, such as generation by neutron absorption of a precursor nuclide in a nuclear reactor, by cyclotron reactions, or by isotopic separation such as by mass spectrometry. The isotopic forms are incorporated into precursors as required for use in any particular synthetic route. For example, $^{14}$C and $^3$H can be prepared using neutrons generated in a nuclear reactor. Following nuclear transformation, $^{14}$C and $^3$H are incorporated into precursor molecules, followed by further elaboration as needed.

When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, which can also be written as "CO", "C(O)", or "C(=O)", wherein the C and the O are double bonded. When a carbon atom is substituted with a double-bonded oxygen (=O) group, the oxygen substituent is termed an "oxo" group. When a divalent substituent such as NR is double-bonded to a carbon atom, the resulting C(=NR) group is termed an "imino" group. When a divalent substituent such as S is double-bonded to a carbon atom, the results C(=S) group is termed a "thiocarbonyl" or "thiono" group.

Alternatively, a divalent substituent such as O or S can be connected by two single bonds to two different carbon atoms. For example, O, a divalent substituent, can be bonded to each of two adjacent carbon atoms to provide an epoxide group, or the O can form a bridging ether group, termed an "oxy" group, between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as $(CH_2)_n$ or $(CR'_2)_n$ wherein n is 1, 2, 3, or more, and each R' is independently selected.

Another divalent substituent is an alkylidene carbon, represented as C= and signifying that the carbon atom so indicated, which also bears two additional groups, is double bonded to a third group. For example, $(CH_3)_2$C= indicates an isopropylidene group bonded to another carbon or nitrogen atom.

C(O) and S(O)$_2$ groups can also be bound to one or two heteroatoms, such as nitrogen or oxygen, rather than to a carbon atom. For example, when a C(O) group is bound to one carbon and one nitrogen atom, the resulting group is called an "amide" or "carboxamide." When a C(O) group is bound to two nitrogen atoms, the functional group is termed a "urea." When a C(O) is bonded to one oxygen and one nitrogen atom, the resulting group is termed a "carbamate" or "urethane." When a S(O)$_2$ group is bound to one carbon and one nitrogen atom, the resulting unit is termed a "sulfonamide." When a $S(O)_2$ group is bound to two nitrogen atoms, the resulting unit is termed a "sulfamide."

Substituted alkyl, alkenyl, alkynyl, cycloalkyl, and cycloalkenyl groups as well as other substituted groups also include groups in which one or more bonds to a hydrogen atom are replaced by one or more bonds, including double or triple bonds, to a carbon atom, or to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups can also be substituted with alkyl, alkenyl, and alkynyl groups as defined herein.

By a "ring system" as the term is used herein is meant a moiety comprising one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic. By "spirocyclic" is meant the class of structures wherein two rings are fused at a single tetrahedral carbon atom, as is well known in the art.

As to any of the groups described herein, which contain one or more substituents, it is understood, of course, that such groups do not contain any substitution or substitution patterns which are sterically impractical and/or synthetically non-feasible. In addition, the compounds of this disclosed subject matter include all stereochemical isomers arising from the substitution of these compounds.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed above, for example, amino, hydroxy, cyano, carboxy, nitro, thio, alkoxy, and halogen groups. Exemplary alkyl groups include, but are not limited to, straight or branched hydrocarbons of 1-6, 1-4, or 1-3 carbon atoms, referred to herein as $C_{1-6}$alkyl, $C_{1-4}$alkyl, and $C_{1-3}$alkyl, respectively. Exemplary alkyl groups include, but are not limited to, methyl, ethyl, propyl, isopropyl, 2-methyl-1-butyl, 3-methyl-2-butyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4- 2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The terms "carbocyclic," "carbocyclyl," and "carbocycle" denote a ring structure wherein the atoms of the ring are carbon, such as a cycloalkyl group or an aryl group. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N–1 substituents wherein N is the size of the carbocyclic ring with, for example, alkyl, alkenyl, alkynyl, amino, aryl, hydroxy, cyano, carboxy, heteroaryl, heterocyclyl, nitro, thio, alkoxy, and halogen groups, or other groups as are listed above. A carbocyclyl ring can be a cycloalkyl ring, a cycloalkenyl ring, or an aryl ring. A carbocyclyl can be monocyclic or polycyclic, and if polycyclic each ring can be independently be a cycloalkyl ring, a cycloalkenyl ring, or an aryl ring.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to vinyl, —CH═CH($CH_3$), —CH═C($CH_3$)$_2$, —C($CH_3$)═$CH_2$, —C($CH_3$)═CH($CH_3$), —C($CH_2CH_3$)═$CH_2$, cyclohexenyl, cyclopentenyl, cyclohexadienyl, butadienyl, pentadienyl, and hexadienyl among others. Exemplary alkenyl groups include, but are not limited to, a straight or branched group of 2-6 or 3-4 carbon atoms, referred to herein as $C_{2-6}$alkenyl, and $C_{3-4}$alkenyl, respectively. Exemplary alkenyl groups include, but are not limited to, vinyl, allyl, butenyl, pentenyl, etc.

Cycloalkenyl groups include cycloalkyl groups having at least one double bond between 2 carbons. Thus for example, cycloalkenyl groups include but are not limited to cyclohexenyl, cyclopentenyl, and cyclohexadienyl groups. Cycloalkenyl groups can have from 3 to about 8-12 ring members, whereas in other embodiments the number of ring carbon atoms range from 3 to 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like, provided they include at least one double bond within a ring. Cycloalkenyl groups also include rings that are substituted with straight or branched chain alkyl groups as defined above.

(Cycloalkenyl)alkyl groups are alkyl groups as defined above in which a hydrogen or carbon bond of the alkyl group is replaced with a bond to a cycloalkenyl group as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

Aryl groups are cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. Aralkenyl group are alkenyl groups as defined above in which a hydrogen or carbon bond of an alkyl group is replaced with a bond to an aryl group as defined above.

Heterocyclyl groups or the term "heterocyclyl" includes aromatic and non-aromatic ring compounds containing 3 or more ring members, of which, one or more is a heteroatom such as, but not limited to, N, O, and S. Thus a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a C$_2$-heterocyclyl can be a 5-ring with two carbon atoms and three heteroatoms, a 6-ring with two carbon atoms and four heteroatoms and so forth. Likewise a C$_4$-heterocyclyl can be a 5-ring with one heteroatom, a 6-ring with two heteroatoms, and so forth. The number of carbon atoms plus the number of heteroatoms sums up to equal the total number of ring atoms. A heterocyclyl ring can also include one or more double bonds. A heteroaryl ring is an embodiment of a heterocyclyl group. The phrase "heterocyclyl group" includes fused ring species including those comprising fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed above. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed above.

Heteroaryl groups are aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heterocyclyl group designated as a C$_2$-heteroaryl can be a 5-ring with two carbon atoms and three heteroatoms, a 6-ring with two carbon atoms and four heteroatoms and so forth. Likewise a C$_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, thiadiazolyl, pyridinyl, pyrimidinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed above. Representative substituted heteroaryl groups can be substituted one or more times with groups such as those listed above.

Heterocyclylalkyl groups are alkyl groups as defined above in which a hydrogen or carbon bond of an alkyl group as defined above is replaced with a bond to a heterocyclyl group as defined above. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

Heteroarylalkyl groups are alkyl groups as defined above in which a hydrogen or carbon bond of an alkyl group is replaced with a bond to a heteroaryl group as defined above.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Exemplary alkoxy groups include, but are not limited to, alkoxy groups of 1-6 or 2-6 carbon atoms, referred to herein as C$_{1-6}$alkoxy, and C$_{2-6}$alkoxy, respectively. Exemplary alkoxy groups include, but are not limited to methoxy, ethoxy, isopropoxy, etc.

An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

The term "cycloalkoxy" as used herein refers to a cycloalkyl group attached to oxygen (cycloalkyl-O—). Examples of cyclic alkoxy include but are not limited to cyclopropyloxy, cyclobutyloxy, cyclopentyloxy, cyclohexyloxy, and the like. Exemplary cycloalkoxy groups include, but are not limited to, cycloalkoxy groups of 3-6 carbon atoms, referred to herein as C$_{3-6}$cycloalkoxy groups. Exemplary cycloalkoxy groups include, but are not limited to, cyclopropoxy, cyclobutoxy, cyclohexyloxy, and the like.

The terms "halo" or "halogen" or "halide" by themselves or as part of another substituent mean, unless otherwise stated, a fluorine, chlorine, bromine, or iodine atom, preferably, fluorine, chlorine, or bromine.

A "haloalkyl" group includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

A "haloalkoxy" group includes mono-halo alkoxy groups, poly-halo alkoxy groups wherein all halo atoms can be the same or different, and per-halo alkoxy groups, wherein all hydrogen atoms are replaced by halogen atoms, such as fluoro. Examples of haloalkoxy include trifluoromethoxy, 1,1-dichloroethoxy, 1,2-dichloroethoxy, 1,3-dibromo-3,3-difluoropropoxy, perfluorobutoxy, and the like.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

An "acyl" group as the term is used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "amine" includes primary, secondary, and tertiary amines having, e.g., the formula $N(group)_3$ wherein each group can independently be H or non-H, such as alkyl, aryl, and the like. Amines include but are not limited to R—NH, for example, alkylamines, arylamines, alkylarylamines; $R_2NH$ wherein each R is independently selected, such as dialkylamines, diarylamines, aralkylamines, heterocyclylamines and the like; and RN wherein each R is independently selected, such as trialkylamines, dialkylarylamines, alkyldiarylamines, triarylamines, and the like. The term "amine" also includes ammonium ions as used herein.

An "amino" group is a substituent of the form —$NH_2$, —NHR, —$NR_2$, —$NR_3^+$, wherein each R is independently selected, and protonated forms of each, except for —$NR_3^+$, which cannot be protonated. Accordingly, any compound substituted with an amino group can be viewed as an amine. An "amino group" within the meaning herein can be a primary, secondary, tertiary or quaternary amino group. An "alkylamino" group includes a monoalkylamino, dialkylamino, and trialkylamino group.

An "ammonium" ion includes the unsubstituted ammonium ion $NH_4^+$, but unless otherwise specified, it also includes any protonated or quaternarized forms of amines. Thus, trimethylammonium hydrochloride and tetramethylammonium chloride are both ammonium ions, and amines, within the meaning herein.

The term "amide" (or "amido") includes C- and N-amide groups, i.e., —$C(O)NR_2$, and —NRC(O)R groups, respectively. Amide groups therefore include but are not limited to primary carboxamide groups (—$C(O)NH_2$) and formamide groups (—NHC(O)H). A "carboxamido" group is a group of the formula $C(O)NR_2$, wherein R can be H, alkyl, aryl, etc.

Standard abbreviations for chemical groups such as are well known in the art are used; e.g., Me=methyl, Et=ethyl, i-Pr=isopropyl, Bu=butyl, t-Bu=tert-butyl, Ph=phenyl, Bn=benzyl, Ac=acetyl, Bz=benzoyl, and the like.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as $NH_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention. "Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of Formula (I) compounds, for example in their purification by recrystallization. All of these salts may be prepared by conventional means from the corresponding compound according to Formula (I) by reacting, for example, the appropriate acid or base with the compound according to Formula (I). The term "pharmaceutically acceptable salts" refers to nontoxic inorganic or organic acid and/or base addition salts, see, for example, Lit et al., Salt Selection for Basic Drugs (1986), *Int J. Pharm.*, 33, 201-217, incorporated by reference herein.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "solvate" is a similar composition except that a solvent other that water replaces the water. For example, methanol or ethanol can form an "alcoholate", which can again be stoichiometric or non-stoichiometric. As the term is used herein a "solvate" refers to a solid form, i.e., a compound in solution in a solvent, while it may be solvated, is not a solvate as the term is used herein.

A "prodrug" as is well known in the art is a substance that can be administered to a patient where the substance is converted in vivo by the action of biochemicals within the patients body, such as enzymes, to the active pharmaceutical ingredient. Examples of prodrugs include esters of carboxylic acid groups, which can be hydrolyzed by endogenous esterases as are found in the bloodstream of humans and other mammals. Conventional procedures for the selection and preparation of suitable prodrug derivatives are described, for example, in "Design of Prodrugs", ed. H. Bundgaard, Elsevier, 1985.

The transformation may occur by various mechanisms (such as by esterase, amidase, phosphatase, oxidative and or reductive metabolism) in various locations (such as in the intestinal lumen or upon transit of the intestine, blood or liver). Prodrugs are well known in the art (for example, see Rautio, Kumpulainen, et al, Nature Reviews Drug Discovery 2008, 7, 255). For example, if a compound of the invention or a pharmaceutically acceptable salt, hydrate or solvate of the compound contains a carboxylic acid functional group, a prodrug can comprise an ester formed by the replacement of the hydrogen atom of the acid group with a group such as $(C_{1-8})$alkyl, $(C_{2-12})$alkylcarbonyloxymethyl, 1-(alkylcarbonyloxy)ethyl having from 4 to 9 carbon atoms, 1-methyl-1-(alkylcarbonyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_{1-2})$alkylamino$(C_{2-3})$alkyl (such as β-dimethylaminoethyl), carbamoyl-$(C_{1-2})$alkyl, N,N-di$(C_{1-2})$alkylcarbamoyl-$(C_{1-2})$alkyl and piperidino-, pyrrolidino- or morpholino$(C_{2-3})$alkyl.

Similarly, if a compound of the invention, or a compound useful in practice of a method of the invention, contains an alcohol functional group, a prodrug can be formed by the replacement of the hydrogen atom of the alcohol group with a group such as $(C_{1-6})$alkylcarbonyloxymethyl, 1-($(C_{1-6})$alkylcarbonyloxy)ethyl, 1-methyl-1-($(C_{1-6})$alkylcarbonyloxy)ethyl $(C_{1-6})$alkoxycarbonyloxymethyl, N—$(C_{1-6})$alkoxycarbonylaminomethyl, succinoyl, $(C_{1-6})$alkylcarbonyl, α-amino$(C_{1-4})$alkylcarbonyl, arylalkylcarbonyl and α-aminoalkylcarbonyl, or α-aminoalkylcarbonyl-α-aminoalkylcarbonyl, where each α-aminoalkylcarbonyl group is independently selected from the naturally occurring L-amino acids, $P(O)(OH)_2$, —$P(O)(O(C_{1-6})alkyl)_2$ or glycosyl (the radical resulting from the removal of a hydroxyl group of the hemiacetal form of a carbohydrate).

Alternatively or additionally, if a compound of the invention, or a compound useful in practice of a method of the invention, incorporates an amine functional group, a prodrug can be formed, for example, by creation of an amide or carbamate, an N-alkylcarbonyloxyalkyl derivative, an (oxodioxolenyl)methyl derivative, an N-Mannich base, imine or enamine. In addition, a secondary amine can be metabolically cleaved to generate a bioactive primary amine, or a tertiary amine can metabolically cleaved to generate a bioactive primary or secondary amine. For examples, see Simplicio, et al., *Molecules* 2008, 13, 519 and references therein.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

In various embodiments, the compound or set of compounds, such as are used in the inventive methods, can be any one of any of the combinations and/or sub-combinations of the above-listed embodiments.

In various embodiments, a compound as shown in any of the Examples, or among the exemplary compounds, is provided. Provisos may apply to any of the disclosed categories or embodiments wherein any one or more of the other above disclosed embodiments or species may be excluded from such categories or embodiments.

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials. All commercially available chemicals were obtained from Aldrich, Alfa Aesare, Wako, Acros, Fisher, Fluka, Maybridge or the like and were used without further purification, except where noted. Dry solvents are obtained, for example, by passing these through activated alumina columns.

The present invention further embraces isolated compounds of the invention. The expression "isolated compound" refers to a preparation of a compound of the invention, or a mixture of compounds the invention, wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used therapeutically. Preferably an "isolated compound" refers to a preparation of a compound of the invention or a mixture of compounds of the invention, which contains the named compound or mixture of compounds of the invention in an amount of at least 10 percent by weight of the total weight. Preferably the preparation contains the named compound or mixture of compounds in an amount of at least 50 percent by weight of the total weight; more preferably at least 80 percent by weight of the total weight; and most preferably at least 90 percent, at least 95 percent or at least 98 percent by weight of the total weight of the preparation.

The compounds of the invention and intermediates may be isolated from their reaction mixtures and purified by standard techniques such as filtration, liquid-liquid extraction, solid phase extraction, distillation, recrystallization or chromatography, including flash column chromatography, or HPLC.

Isomerism and Tautomerism in Compounds of the Invention
Tautomerism

Within the present invention it is to be understood that a compound of the formula (I) or a salt thereof may exhibit the phenomenon of tautomerism whereby two chemical compounds that are capable of facile interconversion by exchanging a hydrogen atom between two atoms, to either of which it forms a covalent bond. Since the tautomeric compounds exist in mobile equilibrium with each other they may be regarded as different isomeric forms of the same compound. It is to be understood that the formulae drawings within this specification can represent only one of the possible tautomeric forms. However, it is also to be understood that the invention encompasses any tautomeric form, and is not to be limited merely to any one tautomeric form utilized within the formulae drawings. The formulae drawings within this specification can represent only one of the possible tautomeric forms and it is to be understood that the specification encompasses all possible tautomeric forms of the compounds drawn not just those forms which it has been convenient to show graphically herein. For example, tautomerism may be exhibited by a pyrazolyl group bonded as indicated by the wavy line. While both substituents would be termed a 4-pyrazolyl group, it is evident that a different nitrogen atom bears the hydrogen atom in each structure.

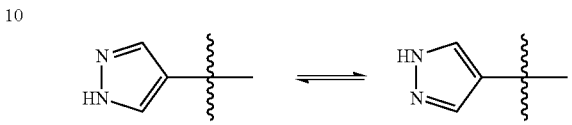

Such tautomerism can also occur with substituted pyrazoles such as 3-methyl, 5-methyl, or 3,5-dimethylpyrazoles, and the like. Another example of tautomerism is amido-imido (lactam-lactim when cyclic) tautomerism, such as is seen in heterocyclic compounds bearing a ring oxygen atom adjacent to a ring nitrogen atom. For example, the equilibrium:

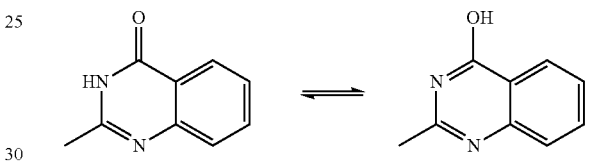

is an example of tautomerism. Accordingly, a structure depicted herein as one tautomer is intended to also include the other tautomer.

Optical Isomerism

It will be understood that when compounds of the present invention contain one or more chiral centers, the compounds may exist in, and may be isolated as single and substantially pure enantiomeric or diastereomeric forms or as racemic mixtures. The present invention therefore includes any possible enantiomers, diastereomers, racemates or mixtures thereof of the compounds of the invention.

The compounds of the invention, or compounds used in practicing methods of the invention, may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The present invention encompasses various stereoisomers of these compounds and mixtures thereof.

Mixtures of enantiomers or diastereomers may be designated "(±)" in nomenclature, but the skilled artisan will recognize that a structure may denote a chiral center implicitly.

The compounds of the disclosure may contain one or more double bonds and, therefore, exist as geometric isomers resulting from the arrangement of substituents around a carbon-carbon double bond. The symbol ═══ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond.

Compounds of the invention, or compounds used in practicing methods of the invention, may contain a carbocyclic or heterocyclic ring and therefore, exist as geometric isomers resulting from the arrangement of substituents around the ring. The arrangement of substituents around a carbocyclic or heterocyclic ring are designated as being in the "Z" or "E" configuration wherein the terms "Z" and "E" are used in accordance with IUPAC standards. Unless otherwise specified, structures depicting carbocyclic or heterocyclic rings encompass both "Z" and "E" isomers. Substituents around a carbocyclic or heterocyclic rings may also be referred to as "cis" or "trans", where the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Individual enantiomers and diastereomers of contemplated compounds can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, *Classics in Stereoselective Synthesis*, Wiley-VCH: Weinheim, 2009.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. The priority of substituents is ranked based on atomic weights, a higher atomic weight, as determined by the systematic procedure, having a higher priority ranking Once the priority ranking of the four groups is determined, the molecule is oriented so that the lowest ranking group is pointed away from the viewer. Then, if the descending rank order of the other groups proceeds clockwise, the molecule is designated as having an (R) absolute configuration, and if the descending rank of the other groups proceeds counterclockwise, the molecule is designated as having an (S) absolute configuration. In the example in the Scheme below, the Cahn-Ingold-Prelog ranking is A>B>C>D. The lowest ranking atom, D is oriented away from the viewer. The solid wedge indicates that the atom bonded thereby projects toward the viewer out of the plane of the paper, and a dashed wedge indicates that the atom bonded thereby projects away from the viewer out of the plan of the paper, i.e., the plane "of the paper" being defined by atoms A, C, and the chiral carbon atom for the (R) configuration shown below.

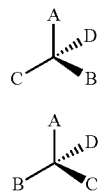

(R) configuration (S) configuration

A carbon atom bearing the A-D atoms as shown above is known as a "chiral" carbon atom, and the position of such a carbon atom in a molecule is termed a "chiral center." Compounds of the invention may contain more than one chiral center, and the configuration at each chiral center is described in the same fashion.

There are various conventions for depicting chiral structures using solid and dashed wedges. For example, for the (R) configuration shown above, the following two depictions are equivalent:

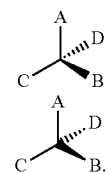

The present invention is meant to encompass diastereomers as well as their racemic and resolved, diastereomerically and enantiomerically pure forms and salts thereof. Diastereomeric pairs may be resolved by known separation techniques including normal and reverse phase chromatography, and crystallization.

"Isolated optical isomer" or "isolated enantiomer" means a compound which has been substantially purified from the corresponding optical isomer(s) of the same formula. Preferably, the isolated isomer is at least about 80%, more preferably at least 90% enantiomerically pure, even more preferably at least 98% enantiomerically pure, most preferably at least about 99% enantiomerically pure, by weight. By "enantiomeric purity" is meant the percent of the predominant enantiomer in an enantiomeric mixture of optical isomers of a compound. A pure single enantiomer has an enantiomeric purity of 100%.

Isolated optical isomers may be purified from racemic mixtures by well-known chiral separation techniques. According to one such method, a racemic mixture of a compound of the invention, or a chiral intermediate thereof, is separated into 99% wt. % pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer's instructions.

Another well-known method of obtaining separate and substantially pure optical isomers is classic resolution, whereby a chiral racemic compound containing an ionized functional group, such as a protonated amine or carboxylate group, forms diastereomeric salts with an oppositely ionized chiral nonracemic additive. The resultant diastereomeric salt forms can then be separated by standard physical means, such as differential solubility, and then the chiral nonracemic additive may be either removed or exchanged with an alternate counter ion by standard chemical means, or alternatively the diastereomeric salt form may retained as a salt to be used as a therapeutic agent or as a precursor to a therapeutic agent.

In various embodiments, the compound or set of compounds, such as are among the inventive compounds or are used in the inventive methods, can be any one of any of the combinations and/or sub-combinations of the above-listed embodiments.

Pharmaceutical Compositions and Methods of Treatment

In various embodiments, the invention provides pharmaceutical compositions comprising a compound of the invention and a pharmaceutically acceptable excipient.

Another aspect of an embodiment of the invention provides compositions of the compounds of the invention, alone or in combination with another medicament. As set forth herein, compounds of the invention include stereoisomers, tautomers, solvates, prodrugs, pharmaceutically acceptable salts and mixtures thereof. Compositions containing a compound of the invention can be prepared by conventional techniques, e.g. as described in Remington: *The Science and Practice of Pharmacy,* 19th Ed., 1995, or later versions thereof, incorporated by reference herein. The compositions can appear in conventional forms, for example capsules, tablets, aerosols, solutions, suspensions or topical applications.

Typical compositions include a compound of the invention and a pharmaceutically acceptable excipient which can be a carrier or a diluent. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents which do not deleteriously react with the active compounds. Such additives can include wetting agents, emulsifying and suspending agents, salt for influencing osmotic pressure, buffers and/or coloring substances preserving agents, sweetening agents or flavoring agents. The compositions can also be sterilized if desired.

The route of administration can be any route which effectively transports the active compound of the invention to the appropriate or desired site of action, such as oral, nasal, pulmonary, buccal, subdermal, intradermal, transdermal or parenteral, e.g., rectal, depot, subcutaneous, intravenous, intraurethral, intramuscular, intranasal, ophthalmic solution or an ointment, the oral route being preferred.

If a solid carrier is used for oral administration, the preparation can be tableted, placed in a hard gelatin capsule in powder or pellet form or it can be in the form of a troche or lozenge. If a liquid carrier is used, the preparation can be in the form of a syrup, emulsion, soft gelatin capsule or sterile injectable liquid such as an aqueous or non-aqueous liquid suspension or solution.

Injectable dosage forms generally include aqueous suspensions or oil suspensions which can be prepared using a suitable dispersant or wetting agent and a suspending agent Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. Preferably, the oil or fatty acid is nonvolatile, including natural or synthetic oils, fatty acids, mono-, di- or tri-glycerides.

For injection, the formulation can also be a powder suitable for reconstitution with an appropriate solution as described above. Examples of these include, but are not limited to, freeze dried, rotary dried or spray dried powders, amorphous powders, granules, precipitates, or particulates. For injection, the formulations can optionally contain stabilizers, pH modifiers, surfactants, bioavailability modifiers and combinations of these. The compounds can be formulated for parenteral administration by injection such as by bolus injection or continuous infusion. A unit dosage form for injection can be in ampoules or in multi-dose containers.

The formulations of the invention can be designed to provide quick, sustained, or delayed release of the active ingredient after administration to the patient by employing procedures well known in the art. Thus, the formulations can also be formulated for controlled release or for slow release.

Compositions contemplated by the present invention can include, for example, micelles or liposomes, or some other encapsulated form, or can be administered in an extended release form to provide a prolonged storage and/or delivery effect. Therefore, the formulations can be compressed into pellets or cylinders and implanted intramuscularly or subcutaneously as depot injections. Such implants can employ known inert materials such as silicones and biodegradable polymers, e.g., polylactide-polyglycolide. Examples of other biodegradable polymers include poly(orthoesters) and poly(anhydrides).

For nasal administration, the preparation can contain a compound of the invention, dissolved or suspended in a liquid carrier, preferably an aqueous carrier, for aerosol application. The carrier can contain additives such as solubilizing agents, e.g., propylene glycol, surfactants, absorption enhancers such as lecithin (phosphatidylcholine) or cyclodextrin, or preservatives such as parabens.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet that can be prepared by conventional tableting techniques can contain:

| Core: | |
|---|---|
| Active compound (as free compound or salt thereof) | 250 mg |
| Colloidal silicon dioxide (Aerosil ®) | 1.5 mg |
| Cellulose, microcryst. (Avicel ®) | 70 mg |
| Modified cellulose gum (Ac-Di-Sol ®) | 7.5 mg |
| Magnesium stearate | Ad. |
| Coating: | |
| HPMC approx. | 9 mg |
| *Mywacett 9-40 T approx. | 0.9 mg |

*Acylated monoglyceride used as plasticizer for film coating.

A typical capsule for oral administration contains compounds of the invention (250 mg), lactose (75 mg) and magnesium stearate (15 mg). The mixture is passed through a 60 mesh sieve and packed into a No. 1 gelatin capsule. A typical injectable preparation is produced by aseptically placing 250 mg of compounds of the invention into a vial, aseptically freeze-drying and sealing. For use, the contents of the vial are mixed with 2 mL of sterile physiological saline, to produce an injectable preparation.

This disclosure provides pharmaceutical compositions comprising compounds as disclosed herein formulated together with a pharmaceutically acceptable carrier. In particular, the present disclosure provides pharmaceutical compositions comprising compounds as disclosed herein formulated together with one or more pharmaceutically acceptable carriers. These formulations include those suitable for oral, rectal, topical, buccal, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral or subcutaneous administration.

The compounds of the invention can be administered to a mammal, especially a human in need of such treatment, prevention, elimination, alleviation or amelioration of a malcondition. Such mammals include also animals, both domestic animals, e.g. household pets, farm animals, and non-domestic animals such as wildlife.

In various embodiments, the invention provides the use of a compound of the invention or of a pharmaceutical composition of the invention for treatment of a disorder for which inhibition of a kinase is medically indicated. For example, the kinase can be a JNK isoform or is LRRK2. For example, the disorder can be Parkinson's disease (PD) Alzheimer's (AD), Huntington's disease (HD), amyotrophic lateral sclerosis (ALS) multiple sclerosis (MS), myocardial infarction (MI), obesity, diabetes, Alzheimer's disease, ALS, Crohn's disease, hearing loss, and conditions where modification of feeding behavior is medically indicated, such as Prader-Willi syndrome.

In various embodiments, the invention provides a method of treatment of a disorder in a patient wherein inhibition of a kinase is medically indicated, comprising administration of an effective dose of a compound of the invention or of the pharmaceutical composition of the invention. For example, the kinase can be a JNK isoform or can be LRRK2. For example, the disorder can be Parkinson's disease (PD) Alzheimer's (AD), Huntington's disease (HD), amyotrophic lateral sclerosis (ALS) multiple sclerosis (MS), myocardial infarction (MI), obesity, diabetes, Alzheimer's disease, ALS, cancer, rheumatoid arthritis, fibrotic disease, pulmonary fibrosis, kidney disease, liver inflammation, Crohn's disease, hearing loss, and conditions where modification of feeding behavior is medically indicated, such as Prader-Willi syndrome.

The compounds of the invention are effective over a wide dosage range. For example, in the treatment of adult humans, dosages from about 0.05 to about 5000 mg, preferably from about 1 to about 2000 mg, and more preferably between about 2 and about 2000 mg per day can be used. A typical dosage is about 10 mg to about 1000 mg per day. In choosing a regimen for patients it can frequently be necessary to begin with a higher dosage and when the condition is under control to reduce the dosage. The exact dosage will depend upon the activity of the compound, mode of administration, on the therapy desired, form in which administered, the subject to be treated and the body weight of the subject to be treated, and the preference and experience of the physician or veterinarian in charge.

Generally, the compounds of the invention are dispensed in unit dosage form including from about 0.05 mg to about 1000 mg of active ingredient together with a pharmaceutically acceptable carrier per unit dosage.

Usually, dosage forms suitable for oral, nasal, pulmonal or transdermal administration include from about 125 µg to about 1250 mg, preferably from about 250 µg to about 500 mg, and more preferably from about 2.5 mg to about 250 mg, of the compounds admixed with a pharmaceutically acceptable carrier or diluent.

Dosage forms can be administered daily, or more than once a day, such as twice or thrice daily. Alternatively dosage forms can be administered less frequently than daily, such as every other day, or weekly, if found to be advisable by a prescribing physician.

Evaluations

It is within ordinary skill to evaluate any compound disclosed and claimed herein for effectiveness in inhibition of JNK/LRRK2 and in the various cellular assays using the procedures described above or found in the scientific literature. Accordingly, the person of ordinary skill can prepare and evaluate any of the claimed compounds without undue experimentation.

Any compound found to be an effective inhibitor of JNK/LRRK2 can likewise be tested in animal models and in human clinical studies using the skill and experience of the investigator to guide the selection of dosages and treatment regimens.

EXAMPLES

The following examples are provided to illustrate the practice of the invention but the invention is not to be interpreted as limited by the examples.

Abbreviations

JNK, c-jun N-terminal kinase; LRRK2, Leucine rich repeat kinase 2; DCM, dichloromethane; DMF, N,N-dimethylformamide; EDC, ethyl-N,N-dimethylaminopropylcarbodiimide; HOBt, N-hydroxybenzotriazole; TFA, trifluoroacetic acid; DIEA, diisopropylethylamine; Boc, tert-butoxycarbonyl; HPLC, high pressure liquid chromatography; MS, mass spectroscopy; NMR, nuclear magnetic spectroscopy; PSA, polar surface area; CNS, central nervous system; DMPK, drug metabolism and pharmacokinetics.

Chemistry

All commercial reagents (Sigma-Aldrich, Fisher, Fluka, Quanta Biochem, Strem, etc.) were used as provided. Anhydrous solvents were purchased and used without further treatments. All reactions were performed under an inert atmosphere of dry Argon in oven-dried (150° C.) glassware. Flash chromatography was performed on an ISCO Combiflash Companion® purification system with prepacked silica gel cartridges and the indicated solvent system. $^1$H NMR and $^{13}$C NMR experiments were recorded on a Bruker 400 MHz or 700 MHz spectrometer. Proton chemical shifts are reported in ppm from an internal standard of residual chloroform (7.26 ppm), methanol (3.31 ppm), or dimethyl sulfoxide (2.50 ppm). Carbon chemical shifts are reported using an internal standard of residual chloroform (77.0 ppm), methanol (49.1 ppm), or dimethyl sulfoxide (39.5 ppm). Proton chemical data are reported as follows: chemical shift, multiplicity (s=singlet, d=doublet, t=triplet, q=quartet, p=pentet, m=multiplet, br=broad), coupling constant, and integration. High resolution mass spectra were acquired on a hybrid linear ion trap-orbitrap instrument (Thermo Scientific) equipped with an ESI interface. Each spectrum was acquired with a resolving power of 100,000 at m/z 400 and was internally calibrated by the addition of caffeine to the sample before analysis.

Synthesis of Bidentate Inhibitors.

Synthesis of compound 6 is presented in Scheme 2. A Suzuki coupling between compounds 9 and 10 was used to give 3-(4'-carboxylphenyl)indazole 11. An $S_N2$ reaction between compound 12 and isobutylamine was applied to yield secondary amine 13, followed by amide formation with Boc-Gly using EDC and HOBt as the coupling reagents to produce 14. After removal of the N-Boc-protection using TFA in dichloromethane, another amide coupling was carried out to give methyl ester 15. Aqueous hydrolysis of 15 using KOH followed by amide formation with N-Boc-hexane-1,6-diamine resulted in compound 16. Finally, Boc-removal by TFA and amide formation with compound 11 yielded compound 6, which was purified by reverse-phase prep HPLC. Similar procedures were also applied to synthesize other compounds in Scheme 1(A), which were all characterized by NMR and MS.

Scheme 2. Synthesis of compound 6$^\alpha$

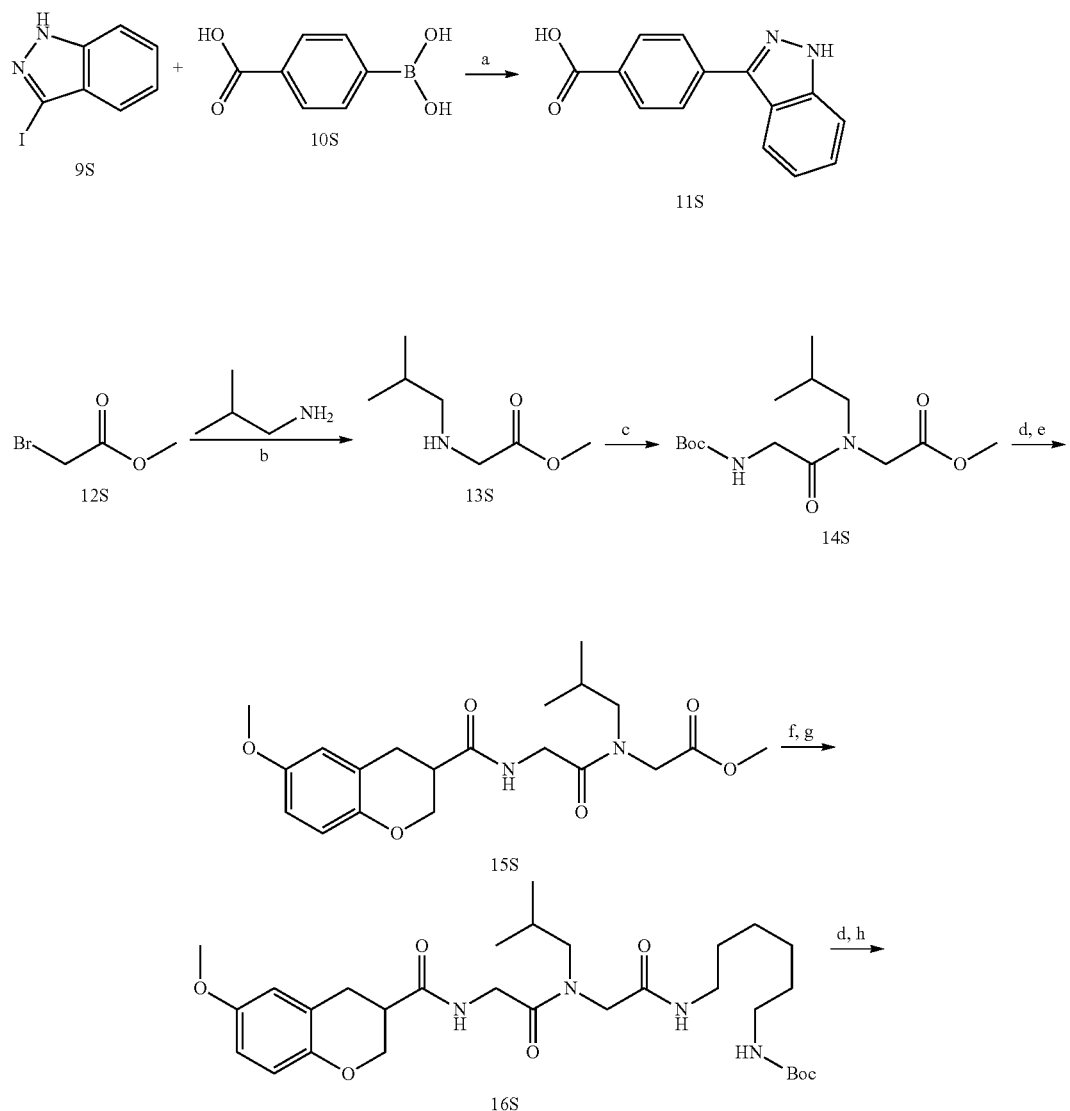

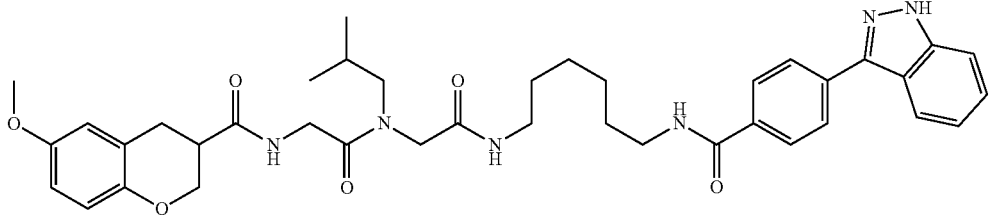

6

"Reagents and conditions: (a) Pd[P(Ph)₃]₄ (10%), K₂CO₃ (5 equiv), 9S (1 equiv), 10S (1.1 equiv), dioxane/H₂O (4:1), 95° C., 4 h. (b) 12S (1 equiv), isobutylamine (1.1 equiv), THF, r.t, 2 h. (c) 13S (1 equiv), Boc-Gly (2 equiv), EDC/HOBt (2 equiv), DIEA (4 equiv), DMF, r.t, overnight. (d) 33% TFA in DCM, r.t, 1 h. (e) acid (1.1 equiv), EDC/HOBt (1.2 equiv), DIEA (2 equiv), DMF, r.t, 2 h. (f) KOH (2 equiv), THF, r.t, 3 h. (g) N-Boc-1,6-hexanediamine (1.2 equiv), EDC/HOBt (1.2 equiv), DIEA (2 equiv), DMF, r.t, 2 h. (h) 11S (1.1 equiv), EDC/HOBt (1.2 equiv), DIEA (2 equiv), DMF, r.t, 2 h.

4-(1H-indazol-3-yl)benzoic acid (11S)

A suspension of 9S (2.44 g, 10 mmol), 10S (1.85 g, 11 mmol), and K₂CO₃ (4.5 g, 33 mmol) in Dioxane/H₂O (4:1) was degassed in a high pressure glass reactor by passing argon for 20 min. After addition of Pd[P(Ph)₃]₄ (1.1 g, 10%), the reactor was sealed and stirred at 95° C. for 4 h, at which LC-MS showed a complete assumption of 9S. The suspension was poured into 400 mL ethyl acetate, washed by saturated NaHCO₃ solution and brine, and dried over anhydrous Na₂SO₄. After the evaporation of solvent in a Rotovapor, the residue was columned in a Combi-Flash system using MeOH/DCM as solvents to give pure titled compound 11S (1.1 g, 46%). MS calculated for C₁₄H₁₀N₂O₂ M+H: 239; observed M+H: 239.

Methyl 2-(isobutylamino)acetate (13S)

Methyl bromoacetate (12S) (3.05 g, 20 mmol) was added drop-wise to a stirred solution of isobutylamine (1.55 g, 22 mmol) and diisopropylethylamine (DIEA, 20 mmol) in THF at r.t and the stirring was continued for additional 4 h. After removal of THF by evaporation in a Rotovapor, the suspension was poured into 500 mL ethyl acetate, washed by saturated NaHCO₃ solution and brine, and dried over anhydrous Na₂SO₄. The solvent was evaporated in a Rotovapor, and the residue was columned using a Combi-Flash system using MeOH/DCM as solvents to give pure titled compound 1S3 (2.5 g, 86%). MS calculated for C₇H₁₅NO₂ M+H: 146; observed M+H: 146.

Methyl 2-(2-((tert-butoxycarbonyl)amino)-N-isobutylacetamido)acetate (14S)

EDC (2.1 g, 11 mmol) was added to a solution of Boc-Gly (1.93 g, 11 mmol), 13S (1.45 g, 10 mmol), HOBt (1.35 g, 10 mmol), and DIEA (3.3 mL, 20 mmol) in DMF, and the suspension was stirred at r.t overnight. The suspension was poured into ethyl acetate (400 mL), washed by saturated NaHCO₃ solution, brine, 1N HCl solution, brine, and dried over Na₂SO₄. The solvent was evaporated in a Rotovapor, and the residue was purified by chromatography (Combi-Flash system) using MeOH/DCM as solvents to give the titled compound 14S (2.2 g, 73%). MS calculated for C₁₄H₂₆N₂O₅ M+H: 303; observed M+H: 303.

Methyl 2-(N-isobutyl-2-(6-methoxychroman-3-carboxamido)acetamido)acetate (15S)

A solution of 14S (0.91 g, 3 mmol) in 30% TFA/DCM was stirred at r.t for 1 h. After evaporation of most TFA and DCM, toluene was applied twice to the residue to remove trace amount of TFA by evaporation in a Rotovapor. The resulting residue was added to a solution of 6-methoxychroman-3-carboxylic acid (0.7 g, 3.3 mmol), EDC (0.8 g, 4 mmol), HOBt (0.5 g, 3.1 mmol), and DIEA (1.65 mL, 10 mmol) in DMF. After stirring at r.t for 2 h, the suspension was poured into ethyl acetate (400 mL), washed by saturated NaHCO₃ solution, brine, 1N HCl solution, brine, and dried over Na₂SO₄. The solvent was evaporated in a Rotovapor, and the residue was purified by chromatography (Combi-Flash system) using MeOH/DCM as solvents to give the titled compound 15S (0.9 g, 77%). MS calculated for C₂₀H₂₈N₂O₆ M+H: 393; observed M+H: 393.

tert-Butyl (6-(2-(N-isobutyl-2-(6-methoxychroman-3-carboxamido)acetamido)acetamido)hexyl)carbamate (16S)

The methyl ester 15S (0.9 g, 2.3 mmol) was suspended in THF/H₂O (4:1) with KOH (0.28 g, 5 mmol) and the suspension was stirred at r.t for 4 h. After removal of THF by evaporation, the aqueous solution (covered by some ethyl acetate) acidified 9 to pH~3) using concentrated HCl, extracted by ethyl acetate twice, and the organic phase was dried over Na₂SO₄. The solvent was evaporated in a Rotovapor to give the corresponding free acid of 15S. tert-Butyl (6-aminohexyl)carbamate (0.54 g, 2.5 mmol) was added to the solution of the newly prepared free acid (2.3 mmol), EDC (0.59 g, 3 mmol), HOBt (0.3 g, 2.2 mmol), and DIEA (0.82 mL, 5 mmol) in DMF. After stirring at r.t for 3 h, the suspension was poured into ethyl acetate (200 mL), washed by saturated NaHCO₃ solution, brine, 1N HCl solution, brine, and dried over Na₂SO₄. The solvent was evaporated in a Rotovapor, and the residue was purified by chromatography (Combi-Flash system) using MeOH/DCM as solvents to give the titled compound 16S (1.1 g, 83%). MS calculated for C₃₀H₄₈N₄O₇ M+H: 577; observed M+H: 577.

N-(2-((2-((6-(4-(1H-indazol-3-yl)benzamido)hexyl)amino)-2-oxoethyl)(isobutyl)amino)-2-oxoethyl)-6-methoxychroman-3-carboxamide (6)

A solution of 16S (1.1 g, 1.9 mmol) in 30% TFA/DCM was stirred at r.t for 1 h. After evaporation of most TFA and DCM, toluene was applied twice to the residue to remove trace amount of TFA by evaporation in a Rotovapor. The resulting residue (120 mg, 0.2 mmol) was added to a solution of 11S (50 mg, 0.22 mmol), EDC (60 mg, 0.3 mmol), HOBt (45 mg, 0.3 mmol), and DIEA (165 □L, 1 mmol) in DMF. After stirring at r.t for 2 h, at which LC-MS analysis showed a complete amide formation, the suspension was directly subjected to reverse phase HPLC purification to obtain the final pure compound 6 as a white solid in its TFA salt form after lyophilization (45 mg, 25%). MS calculated for $C_{39}H_{48}N_6O_6$ M+H: 697; observed M+H: 697. HRMS (M+H) calculated 697.3714, observed 697.3709. $^1$H NMR (400 MHz, DMSO-$d_6$) δ 13.36 (br. s, 1H), 8.51 (t, J=5.68 Hz, 1H), 8.02-8.14 (m, 3H), 7.95-8.01 (m, 2H), 7.62 (td, J=0.82, 8.46 Hz, 1H), 7.43 (ddd, J=0.88, 7.01, 8.27 Hz, 1H), 7.24 (ddd, J=0.88, 6.95, 8.08 Hz, 1H), 6.61-6.71 (m, 3H), 4.18-4.27 (m, 1H), 3.81 (t, J=10.23 Hz, 1H), 3.29 (q, J=6.57 Hz, 2H), 3.01-3.15 (m, 2H), 2.86-2.99 (m, 1H), 2.68-2.82 (m, 2H), 1.32-1.38 (m, 1H), 1.26-1.65 (m, 7H), 0.81 (d, J=6.57 Hz, 1H). $^{13}$C NMR (101 MHz, DMSO-$d_6$) δ 171.1, 165.8, 152.9, 147.6, 133.6, 127.8, 126.3, 121.3, 120.6, 120.1, 116.6, 114.1, 67.2, 55.3, 38.4, 29.0, 27.9, 26.2.

(S)—N1-((S)-1-((2-((4-(4-(1H-indazol-3-yl)benzamido)butyl)amino)-2-oxoethyl)amino)-4-methyl-1-oxopentan-2-yl)-2-((S)-2-acetamido-4-methylpentanamido)succinamide (3)

The tri-peptide Ac-LNL-OH was synthesized first using traditional peptide step-wise synthesis. From this tri-peptide, procedures similar to those applied in Scheme 1 were utilized to prepare the final compound 3 which was purified by reverse phase HPLC to give the final pure compound 3 as a white solid in its TFA salt form after lyophilization. A single peak was detected in analytical HPLC traces based on UV (254 nM) observation. MS calculated for $C_{38}H_{53}N_9O_7$ M+H: 748; observed M+H: 748. HRMS (M+H) calculated 748.4147, observed 748.4140.

N-(2-((2-((6-(4-(1H-indazol-3-yl)benzamido)hexyl)amino)-2-oxoethyl)(isobutyl)amino)-2-oxoethyl)-2,3-dihydrobenzo[b][1,4]dioxine-6-carboxamide (4)

Similar procedures as applied in the synthesis of 6 were also utilized to prepare compound 4. After reverse phase HPLC purification, a single peak was detected in analytical HPLC traces based on UV (254 nM) observation. MS calculated for $C_{37}H_{44}N_6O_6$ M+H: 669; observed M+H: 669. HRMS (M+H) calculated 669.3401, observed 669.3394. $^1$H NMR (400 MHz, DMSO) δ 13.38 (s, 1H), 8.53 (d, J=3.5 Hz, 1H), 8.39 (t, J=5.4 Hz, 1H), 8.13 (d, J=8.3 Hz, 1H), 8.09 (d, J=8.4 Hz, 2H), 7.98 (d, J=8.5 Hz, 2H), 7.74 (d, J=5.5 Hz, 1H), 7.62 (d, J=8.4 Hz, 1H), 7.44 (d, J=7.0 Hz, 1H), 7.39 (td, J=5.5, 2.1 Hz, 2H), 7.25 (t, J=7.4 Hz, 1H), 6.91 (dd, J=8.4, 4.1 Hz, 1H), 4.27 (q, J=4.9 Hz, 4H), 4.11 (d, J=5.7 Hz, 1H), 4.06 (d, J=5.5 Hz, 1H), 4.02 (s, 2H), 3.86 (s, 1H), 3.33-3.23 (m, 2H), 3.18 (d, J=7.3 Hz, 1H), 3.16-3.01 (m, 3H), 1.92 (s, 1H), 1.87-1.77 (m, 1H), 1.54 (d, J=6.4 Hz, 2H), 1.48-1.38 (m, 2H), 1.33 (d, J=8.8 Hz, 4H), 0.91 (d, J=6.6 Hz, 3H), 0.81 (d, J=6.6 Hz, 3H).

N-(2-((2-((6-(4-(1H-indazol-3-yl)benzamido)hexyl)amino)-2-oxoethyl)(isobutyl)amino)-2-oxoethyl)-2,3-dihydrobenzo[b][1,4]dioxine-2-carboxamide (5)

Similar procedures as applied in the synthesis of 6 were also utilized to prepare compound 5. After reverse phase HPLC purification, a single peak was detected in analytical HPLC traces based on UV (254 nM) observation. MS calculated for $C_{37}H_{44}N_6O_6$ M+H: 669; observed M+H: 669. HRMS (M+H) calculated 669.3401, observed 669.3391. $^1$H NMR (400 MHz, DMSO) δ 13.38 (s, 1H), 8.52 (t, J=5.6 Hz, 1H), 8.12 (d, J=8.3 Hz, 2H), 8.08 (d, J=8.6 Hz, 2H), 7.98 (d, J=8.5 Hz, 2H), 7.62 (d, J=8.4 Hz, 1H), 7.46-7.39 (m, 1H), 7.27-7.22 (m, 1H), 7.00-6.95 (m, 1H), 6.90-6.83 (m, 3H), 4.76 (dd, J=6.0, 2.7 Hz, 1H), 4.32 (dd, J=11.5, 2.8 Hz, 1H), 4.20 (dd, J=11.5, 6.1 Hz, 2H), 3.95 (d, J=45.6 Hz, 5H), 3.26 (dd, J=12.9, 6.8 Hz, 2H), 3.18-3.04 (m, 2H), 1.50 (d, J=7.2 Hz, 2H), 1.46-1.36 (m, 2H), 1.33-1.15 (m, 4H).

N—((S)-1-((2-((6-(4-(1H-indazol-3-yl)benzamido)hexyl)amino)-2-oxoethyl)(isobutyl)amino)-1-oxopropan-2-yl)-6-methoxychroman-3-carboxamide (7)

Similar procedures as applied in the synthesis of 6 were also utilized to prepare compound 7. After reverse phase HPLC purification, a single peak was detected in analytical HPLC traces based on UV (254 nM) observation. MS calculated for $C_{40}H_{50}N_6O_6$ M+H: 711; observed M+H: 711. HRMS (M+H) calculated 711.3871, observed 711.3867. $^1$H NMR (DMSO-d6, 400 MHz) δ 13.37 (s, 1H), 8.49 (dd, J=17.0, 9.6 Hz, 2H), 8.10 (dd, J=16.4, 8.2 Hz, 4H), 7.98 (d, J=8.4 Hz, 2H), 7.42 (dd, J=11.3, 3.9 Hz, 1H), 7.27-7.21 (m, 1H), 6.66 (t, J=3.6 Hz, 4H), 4.73-4.65 (m, 1H), 4.57 (d, J=6.9 Hz, 1H), 4.34 (dd, J=17.5, 11.9 Hz, 1H), 4.17 (dd, J=21.4, 9.4 Hz, 2H), 3.66 (t, J=2.8 Hz, 4H), 3.27 (s, 3H), 3.18 (dd, J=13.1, 7.4 Hz, 1H), 3.09 (d, J=6.4 Hz, 3H), 2.97 (d, J=5.1 Hz, 1H), 2.88 (dd, J=19.9, 14.7 Hz, 3H), 2.80-2.65 (m, 2H), 1.84 (d, J=7.1 Hz, 2H), 1.55 (s, 2H), 1.41 (s, 3H), 1.31 (s, 4H), 1.20 (dd, J=9.7, 6.8 Hz, 4H), 0.86 (dd, J=7.8, 5.9 Hz, 3H), 0.79 (ddd, J=13.1, 6.8, 4.3 Hz, 5H).

N-(6-(2-(N-isobutyl-2-(6-methoxychroman-3-carboxamido)acetamido)acetamido)hexyl)-1H-indazole-5-carboxamide (8)

Similar procedures as applied in the synthesis of 6 were also utilized to prepare compound 8. After reverse phase HPLC purification, a single peak was detected in analytical HPLC traces based on UV (254 nM) observation. MS calculated for $C_{33}H_{44}N_6O_6$ M+H: 621; observed M+H: 621. HRMS (M+H) calculated 621.3401, observed 621.3396.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A bidentate kinase inhibitor compound of formula (I)

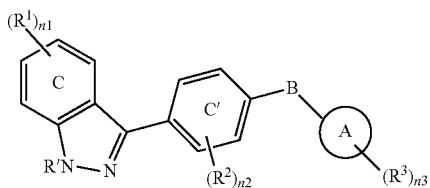

wherein
each of ring C and ring C', is a phenyl ring;
group A is any one of

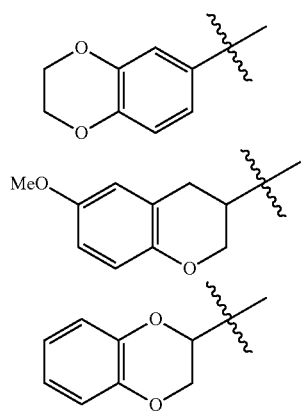

wherein a wavy line indicates a point of bonding;
$R^1$, $R^2$, and $R^3$ are each independently at each occurrence OR, $NR_2$, CN, $CF_3$, halo, or a $(C_{1-6})$alkyl optionally comprising therein any of NR', $S(O)_q$, O, C(=S), C(=O), C(=O)O, OC(=O)O, C(=O)C(=O), C(=O)NR', O(C=O)NR', NR'C(=O)NR', SO2NR', or C(=O)NR'NR';
n1=0, 1, 2, or 3; n2=0, 1, 2, or 3; n3=0, 1, 2, 3, 4, or 5;
R is H, $(C_{1-6})$alkyl, or $(C_{1-6})$acyl;
R' is H, $(C_{1-6})$alkyl, or $(C_{1-6})$acyl; or R' is a 5-16 membered saturated, partially unsaturated, or aromatic, mono-, bi-, or tricyclic ring system, comprising 0-8 heteroatoms selected from the group consisting of O, N, and $S(O)_q$ wherein q=0, 1, or 2, substituted, with n4 $R^4$ groups;
B is a linker wherein B is any one of:

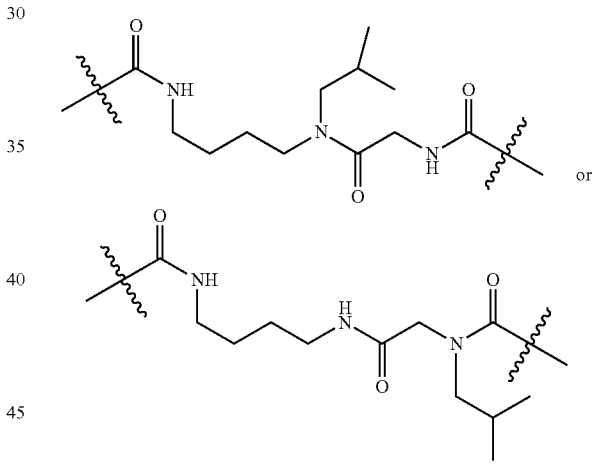

wherein the wavy lines indicate points of bonding to groups A and C, in either orientation;
or a pharmaceutically acceptable salt thereof, or a hydrate, solvate, or prodrug thereof.

2. A compound wherein in the compound is any one of the following:

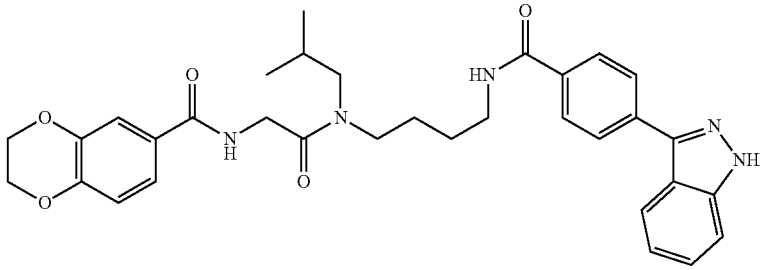

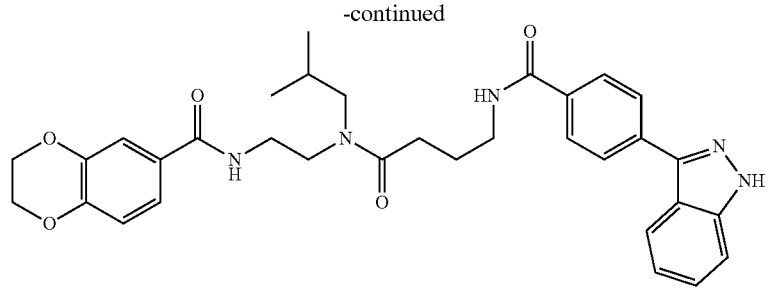
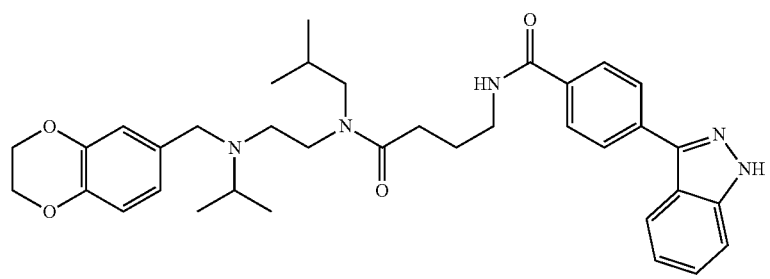
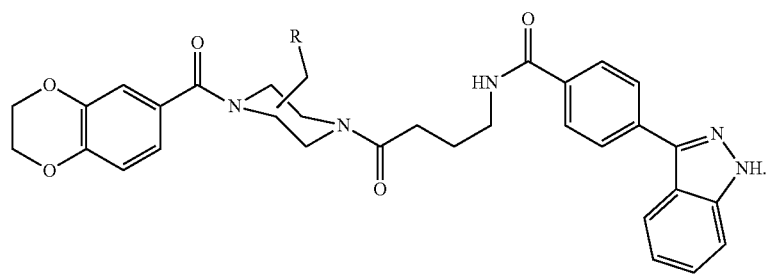
3. A compound wherein the compound is any one of:
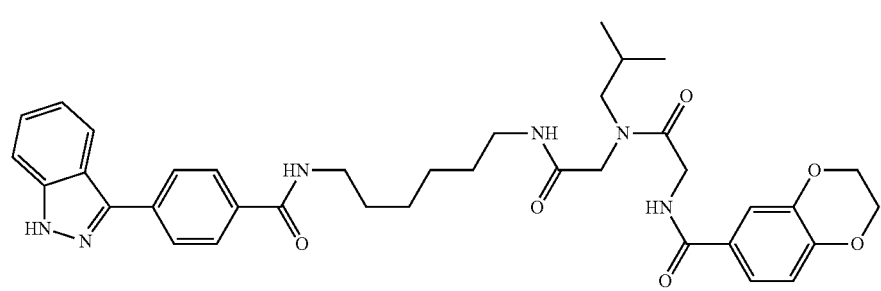
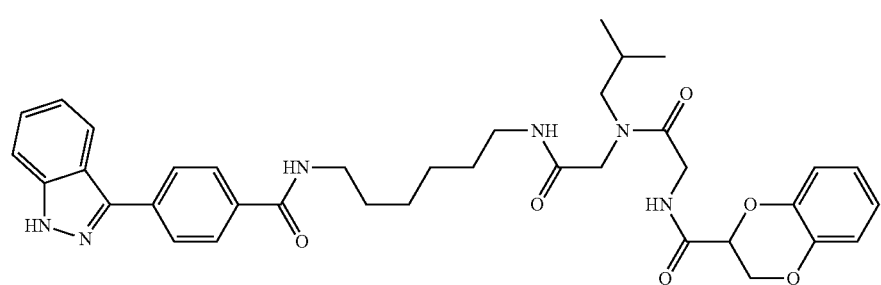

6
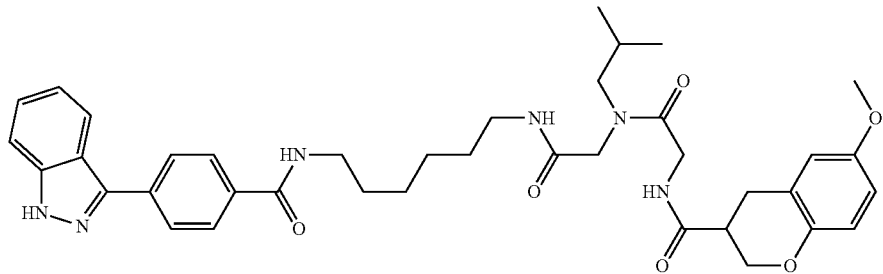
7
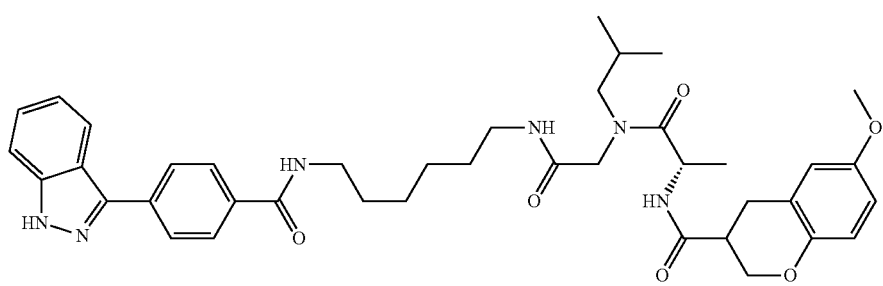
8
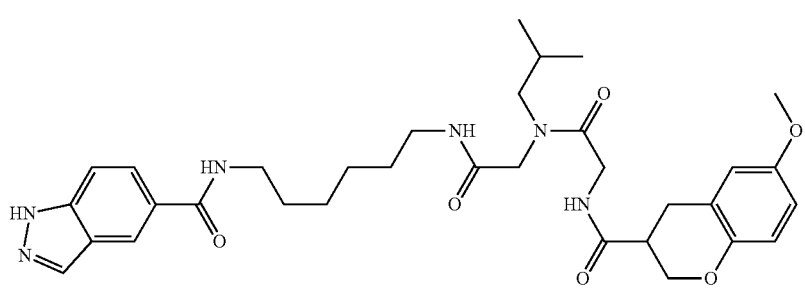
9
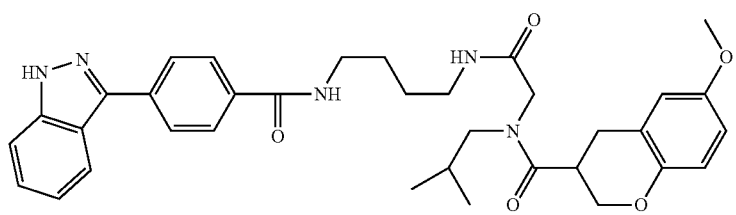
10
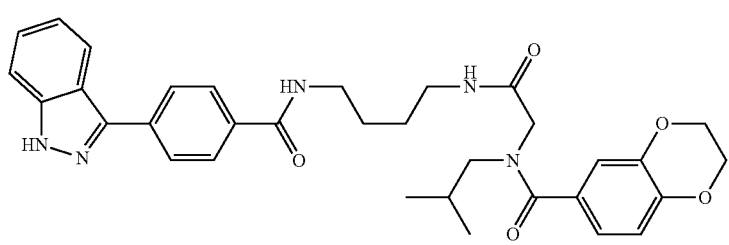
11
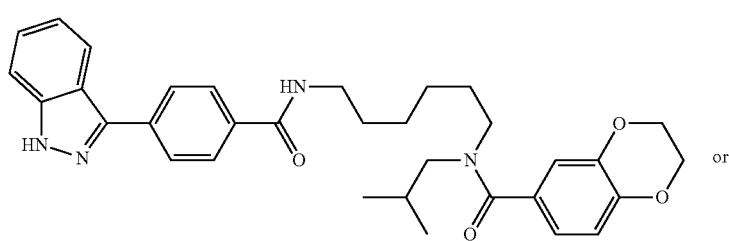 or -continued

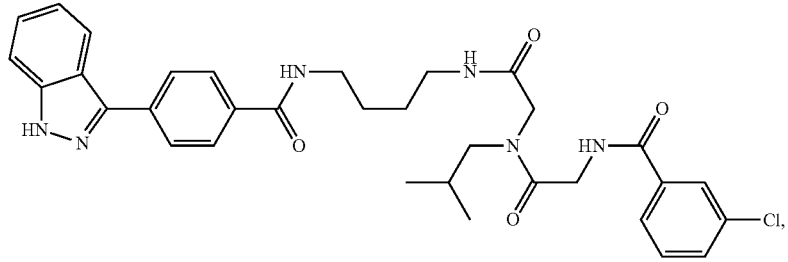

12 or a pharmaceutically acceptable salt thereof, or a hydrate, solvate, or prodrug thereof.

4. A pharmaceutical composition comprising the compound of claim 1 and a pharmaceutically acceptable excipient.

5. A method of treatment of a disorder in a patient wherein inhibition of a kinase is medically indicated, comprising administration of an effective dose of a compound of claim 1.

6. The method of claim 5 wherein the kinase is a JNK isoform or is LRRK2.

7. The method of claim 6 wherein the disorder is Parkinson's disease (PD) Alzheimer's (AD), Huntington's disease (HD), amyotrophic lateral sclerosis (ALS) multiple sclerosis (MS), myocardial infarction (MI), obesity, diabetes, Alzheimer's disease, ALS, Crohn's disease, hearing loss, or Prader-Willi syndrome, or a condition where modification of feeding behavior is medically indicated.

* * * * *

SEQUENCE LISTING

<160> NUMBER OF SEQ ID NOS: 1

<210> SEQ ID NO 1
<211> LENGTH: 11
<212> TYPE: PRT
<213> ORGANISM: Artificial sequence
<220> FEATURE:
<223> OTHER INFORMATION: Synthetic sequence

<400> SEQUENCE: 1

Arg Pro Lys Arg Pro Thr Thr Leu Asn Leu Phe
1               5                   10